United States Patent
Yamada

(10) Patent No.: US 9,726,584 B2
(45) Date of Patent: Aug. 8, 2017

(54) SAMPLE IMAGING APPARATUS

(75) Inventor: Kazuhiro Yamada, Kobe (JP)

(73) Assignee: SYSMEX CORPORATION, Kobe-shi (JP)

(*) Notice: Subject to any disclaimer, the term of this patent is extended or adjusted under 35 U.S.C. 154(b) by 1131 days.

(21) Appl. No.: 12/540,936

(22) Filed: Aug. 13, 2009

(65) Prior Publication Data

US 2010/0074506 A1 Mar. 25, 2010

(30) Foreign Application Priority Data

Sep. 24, 2008 (JP) ................. 2008-244880

(51) Int. Cl.
| | | |
|---|---|---|
| *G06K 9/00* | (2006.01) | |
| *G01N 1/31* | (2006.01) | |
| *G01N 15/14* | (2006.01) | |
| *G01N 35/00* | (2006.01) | |
| *G06T 7/00* | (2017.01) | |
| *G01N 15/00* | (2006.01) | |
| *G01N 15/10* | (2006.01) | |

(52) U.S. Cl.
CPC .......... *G01N 1/312* (2013.01); *G01N 15/1475* (2013.01); *G01N 35/00029* (2013.01); *G01N 35/00722* (2013.01); *G06K 9/00134* (2013.01); *G06K 9/00147* (2013.01); *G06T 7/0012* (2013.01); *G01N 2015/008* (2013.01); *G01N 2015/1068* (2013.01); *G01N 2035/00039* (2013.01); *G06T 2207/10056* (2013.01); *G06T 2207/30024* (2013.01)

(58) Field of Classification Search
CPC . G01N 15/14; G01N 15/1475; G01N 15/1459
See application file for complete search history.

(56) References Cited

U.S. PATENT DOCUMENTS

| | | | |
|---|---|---|---|
| 3,999,047 A | | 12/1976 | Green |
| 4,761,075 A | * | 8/1988 | Matsushita et al. ............ 356/39 |
| 5,281,517 A | * | 1/1994 | Bacus et al. .................. 435/6.12 |
| 5,449,622 A | * | 9/1995 | Yabe et al. ....................... 436/63 |
| 5,768,412 A | * | 6/1998 | Mitsuyama et al. ........... 382/173 |
| 5,850,465 A | * | 12/1998 | Shimura et al. ............... 382/132 |
| 6,137,899 A | * | 10/2000 | Lee et al. ....................... 382/133 |
| 6,376,837 B1 | * | 4/2002 | Itabashi ................... B41J 2/471 250/205 |
| 7,390,997 B2 | * | 6/2008 | Tohma ........................ 250/201.3 |
| 2002/0016620 A1 | * | 2/2002 | Tsujita ..................... A61N 1/08 607/88 |

(Continued)

FOREIGN PATENT DOCUMENTS

| | | |
|---|---|---|
| CN | 1880942 | 12/2006 |
| EP | 1770428 A1 | 4/2007 |

(Continued)

*Primary Examiner* — Elaine Gort
*Assistant Examiner* — Trang Nguyen
(74) *Attorney, Agent, or Firm* — Mots Law, PLLC

(57) ABSTRACT

A sample imaging apparatus comprising: an imaging section for imaging a stained sample including a stained cell to generate a cell image relating to the stained cell included in the stained sample; and a staining abnormality detector for detecting an abnormality relating to staining of the stained sample on the basis of the cell image generated by the imaging section, is disclosed. A sample imaging apparatus comprising: an imaging section for imaging a stained sample to generate a cell image relating to a cell included in the stained sample; and an imaging abnormality detector for detecting an abnormality relating to the imaging section on the basis of the cell image generated by the imaging section, is also disclosed.

19 Claims, 23 Drawing Sheets

(56) References Cited

U.S. PATENT DOCUMENTS

| | | | |
|---|---|---|---|
| 2003/0072484 A1* | 4/2003 | Kokko | G06K 9/00127 |
| | | | 382/155 |
| 2003/0081822 A1* | 5/2003 | Takeo et al. | 382/132 |
| 2004/0252876 A1 | 12/2004 | Wong et al. | |
| 2005/0265588 A1* | 12/2005 | Gholap et al. | 382/128 |
| 2007/0013906 A1 | 1/2007 | Kawate | |
| 2007/0014460 A1* | 1/2007 | Kuziela et al. | 382/128 |
| 2007/0159687 A1* | 7/2007 | Tohma | G02B 21/365 |
| | | | 359/368 |
| 2008/0030732 A1* | 2/2008 | Yaroslavsky et al. | 356/369 |
| 2009/0048785 A1* | 2/2009 | Katzir | G06K 9/00134 |
| | | | 702/20 |
| 2009/0074282 A1* | 3/2009 | Pinard | G06K 9/00127 |
| | | | 382/133 |
| 2009/0091746 A1* | 4/2009 | Fukuda et al. | 356/73 |
| 2009/0190821 A1* | 7/2009 | Marugame | 382/133 |
| 2009/0269799 A1* | 10/2009 | Winkelman | G01N 1/2813 |
| | | | 435/29 |
| 2010/0027868 A1* | 2/2010 | Kosaka | G01N 33/4905 |
| | | | 382/134 |

FOREIGN PATENT DOCUMENTS

| | | |
|---|---|---|
| JP | 62-135767 A | 6/1987 |
| JP | 2001-211896 | 8/2001 |
| JP | 2005-121925 | 5/2005 |
| JP | 2005121925 A | 5/2005 |
| JP | 2007-068460 | 3/2007 |

\* cited by examiner

FIG.4B

| WHITE BLOOD CELL ID (F21) | BLOOD CELL TYPE (F22) | OBJECT OF RECONFIRMATION (F23) |
|---|---|---|
| W001 | NEUT | 0 |
| W002 | BASO | 0 |
| W003 | NEUT | 0 |
| W004 | — | 1 |
| ⋮ | ⋮ | ⋮ |

SPECIMEN ID = 0003

DB2

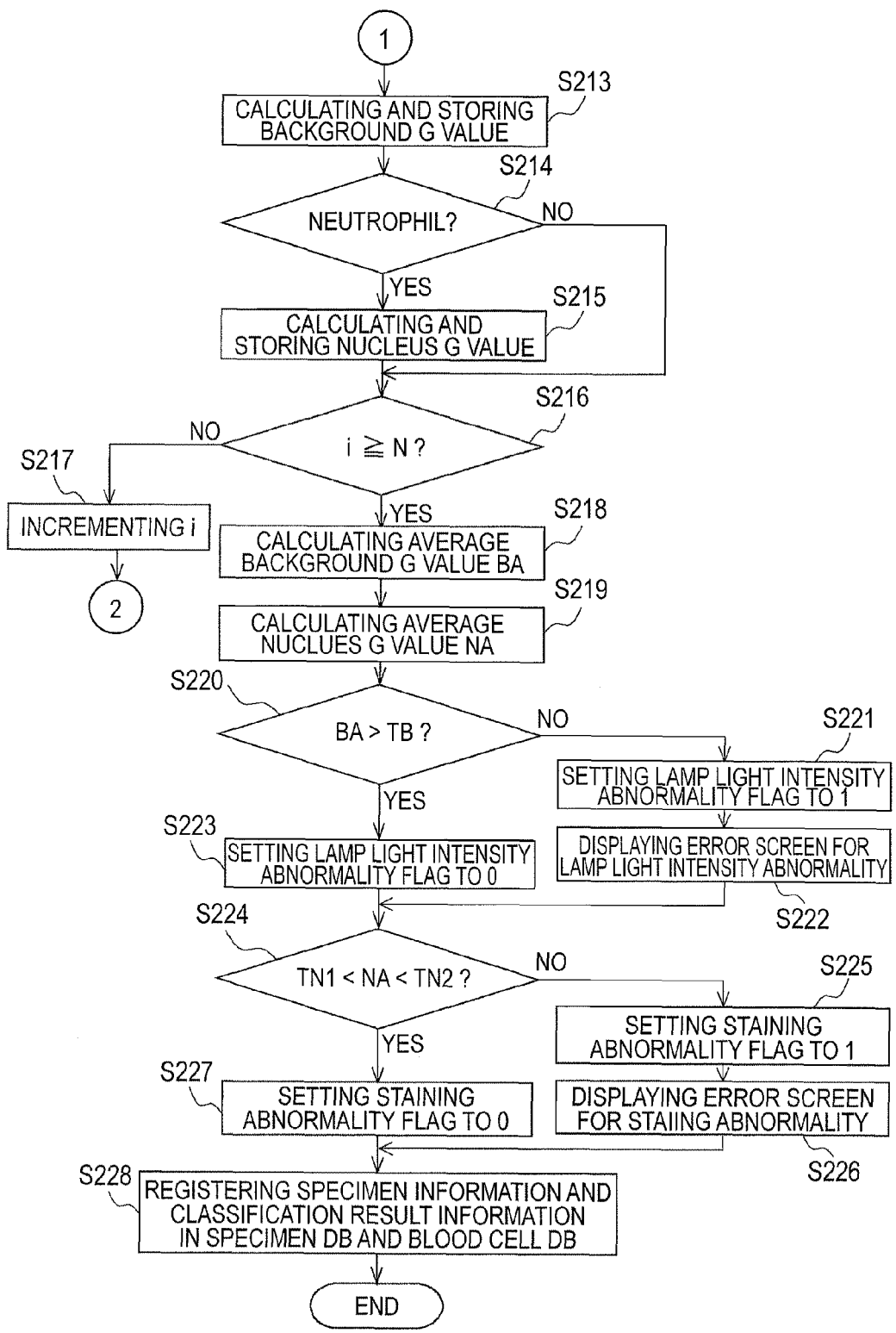

SAMPLE IMAGING APPARATUS

FIELD OF THE INVENTION

The present invention relates to a sample imaging apparatus which images a stained sample and detects abnormalities relating to the staining of the stained sample or abnormalities relating to an imaging section on the basis of the image obtained by the imaging operation.

BACKGROUND

Conventionally, there are known sample imaging apparatuses which image stained blood smears magnified by a microscope and analyze the obtained image to classify blood cells and perform a counting operation.

JP-A-S62-135767 discloses a cell classifying apparatus which performs classification into white blood cells and red blood cells from an image obtained by imaging a sample which is prepared by subjecting a specimen to general staining (May-Giemsa staining), counts the number of reticulocytes from an image obtained by imaging a sample which is prepared by subjecting the specimen to supravital staining, and detects abnormal white blood cells from an image obtained by imaging a sample which is prepared by subjecting the specimen to peroxidase staining. If data of all the stained samples is in a normal range, the cell classifying apparatus classifies the specimen as a normal specimen group, and if various stain data of the same specimen is not in the normal range, the cell classifying apparatus determines whether precise analysis is required such as whether abnormal blood cells have been detected or whether unknown cells exist whose numbers are equal to or more than a certain value. In addition, for a quasi-positive specimen in a mixed area which is difficult to judge as normal or abnormal, the cell classifying apparatus performs a precise automatic re-examination to raise the precision of the analysis.

In the above-described sample imaging apparatus, the blood cell classification operation, the counting operation and the like cannot be normally performed if a blood smear is not normally stained. However, in the cell classifying apparatus disclosed in JP-A-S62-135767, when data of stained samples has an abnormality due to an abnormality in the staining, it is not possible to specify that the abnormality in the data of the stained samples is due to the abnormality in the staining.

SUMMARY OF THE INVENTION

The scope of the present invention is defined solely by the appended claims, and is not affected to any degree by the statements within this summary.

A first aspect of the present invention is a sample imaging apparatus comprising: an imaging section for imaging a stained sample including a stained cell to generate a cell image relating to the stained cell included in the stained sample; and a staining abnormality detector for detecting an abnormality relating to staining of the stained sample on the basis of the cell image generated by the imaging section.

A second aspect of the present invention is a sample imaging apparatus comprising: an imaging section for imaging a stained sample to generate a cell image relating to a cell included in the stained sample; and an imaging abnormality detector for detecting an abnormality relating to the imaging section on the basis of the cell image generated by the imaging section.

BRIEF DESCRIPTION OF THE DRAWINGS

FIG. 4B is a schematic diagram showing the configuration of a blood cell database according to the embodiment;

FIG. 7B is a flowchart (second half) showing the procedure of an operation of the image processing unit in the blood cell image registration operation;

DETAILED DESCRIPTION OF THE PREFERRED EMBODIMENTS

The preferred embodiments of the present invention will be described hereinafter with reference to the drawings.

This embodiment is a sample imaging apparatus which images a stained blood smear magnified by a microscope and processes the blood cell image obtained in this manner to detect abnormalities relating to the staining of the blood smear.

[Configuration of Sample Imaging Apparatus]

Figure 1:
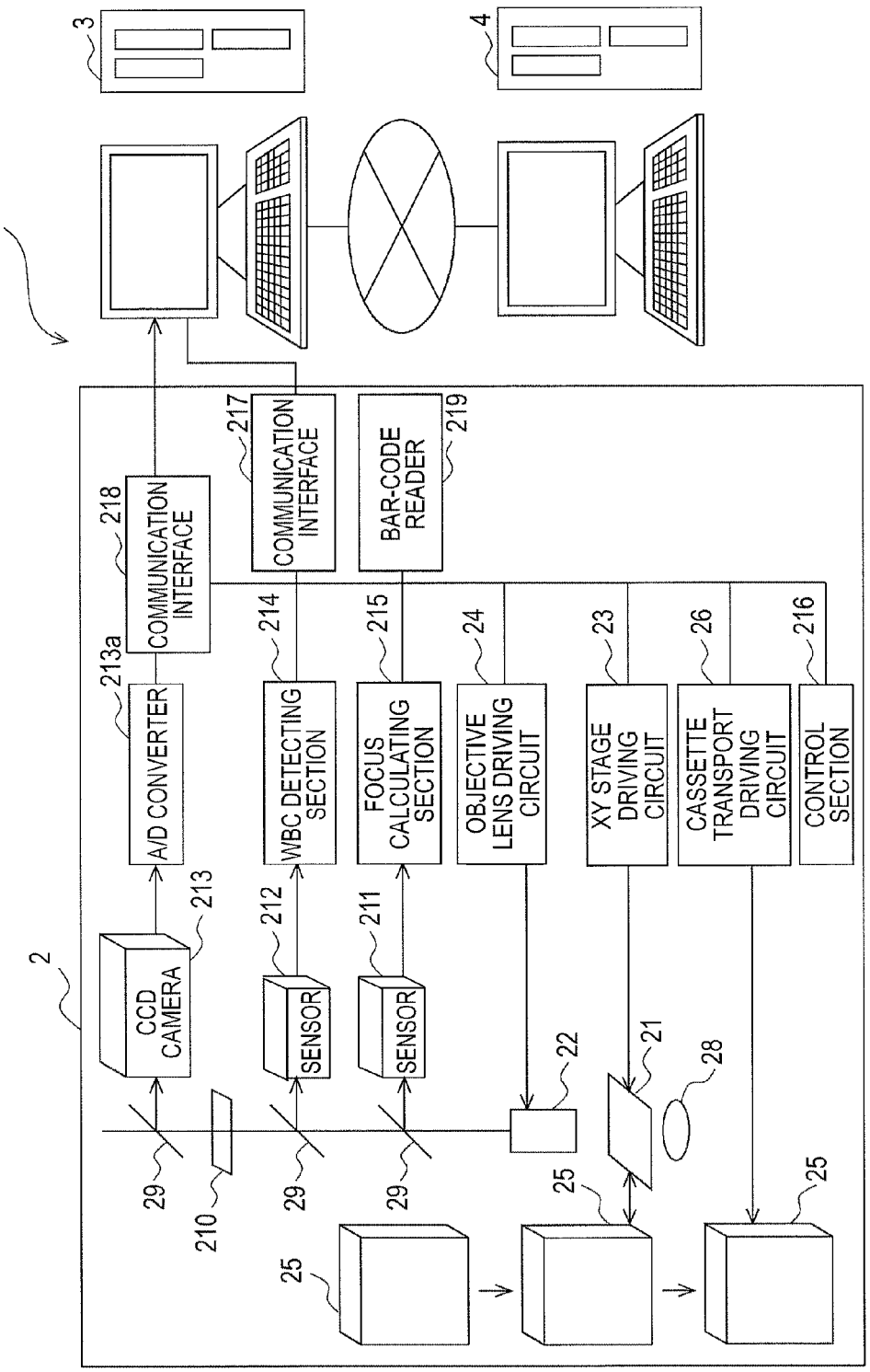
FIG. 1 is a block diagram showing the configuration of a sample imaging apparatus according to an embodiment.

FIG. 1 is a block diagram showing the configuration of the sample imaging apparatus according to this embodiment. FIG. 1 schematically shows the configuration of the apparatus. The arrangement of sensors, a slide cassette and the like may be slightly different from the actual arrangement to enable an easier understanding. For example, in FIG. 1, a sensor for WBC detection and a sensor for auto-focusing are respectively arranged on the upper and lower sides. However, in fact, as shown in FIG. 2 to be described later, both of the sensors are arranged in substantially the same plane.

A sample imaging apparatus 1 includes a microscope unit 2 for imaging a magnified image of a blood smear which is focused by auto-focusing, an image processing unit 3 for processing a captured image to classify white blood cells in blood and performing a counting operation for each classification of the white blood cell, and a blood cell image display unit 4 which is connected to the image processing unit 3 and displays the captured image and analysis results. The image processing unit 3 and the blood cell image display unit 4 may be formed integrally, and not separately, with each other. A smear preparing apparatus (not shown) (for example, a smear preparing apparatus SP-1000i made by Sysmex Corporation) is disposed near the sample imaging apparatus 1 and a blood smear prepared by the smear preparing apparatus is automatically supplied to the microscope unit 2.

<Configuration of Microscope Unit 2>

Figure 2:
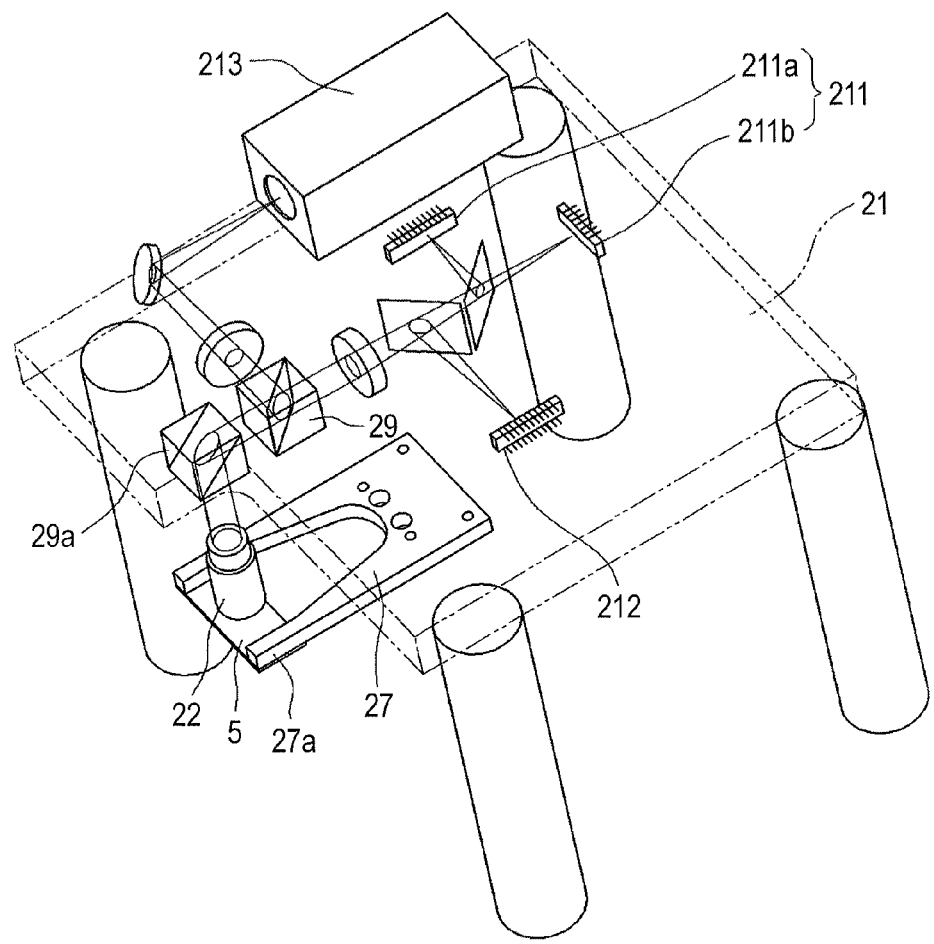
FIG. 2 is a perspective view showing a portion of a microscope unit according to the embodiment.

FIG. 2 is a perspective view showing a portion of the microscope unit 2. The microscope unit 2 includes an objective lens 22 which is a portion of a lens system of a microscope magnifying the image of blood thinly spread and applied over a slide glass 5 mounted on an XY stage 21. The XY stage 21 holding a sample (the slide glass 5 with an upper surface on which the blood is smeared) can be moved back and forth and from side to side (X and Y directions) by a driving section (not shown), the driving of which is controlled by an XY stage driving circuit 23 (see FIG. 1 for reference). The objective lens 22 can be moved up and down (Z direction) by a driving section (not shown), the driving of which is controlled by an objective lens driving circuit 24.

A plurality of the slide glasses 5 are stacked and accommodated in a slide cassette 25. The slide cassette 25 is transported by a transport section (not shown), the driving of which is controlled by a cassette transport driving circuit 26. The XY stage 21 is provided with a chuck section 27 (see FIG. 2 for reference) capable of holding two parts in the vicinities of both ends in the longitudinal direction of the slide glass 5, and the chuck section can be freely advanced and retracted with respect to the slide glass 5 accommodated in the slide cassette 25 which is stopped at a predetermined position. The chuck section 27 is advanced toward the slide cassette 25 to hold the slide glass 5 by an open-close operation of claw sections 27a which can be freely opened and closed and each of which is formed at the tip of the chuck section 27. Then, the chuck section 27 is retracted to draw the slide glass 5 from the slide cassette 25 so that the slide glass can be disposed at a predetermined position on the XY stage 21.

Returning to FIG. 1, a lamp 28 as a light source is disposed below the slide glass 5, and light from the lamp 28 passes through the blood on the slide glass 5, and via half mirrors 29 and an interference filter 210 arranged on an optical path, enters a line sensor 211 for auto-focusing in which plural pixels are arranged in a line, a sensor 212 for white blood cell (WBC) detection in which plural pixels are arranged in a line and a CCD camera 213. A white blood cell detecting section 214 composed of FPGA, ASIC or the like is connected to the sensor 212 for white blood cell detection and is set up to provide the output signal of the sensor 212 to the white blood cell detecting section 214. A focus calculating section 215 composed of FPGA, ASIC or the like is connected to the sensor 211 for auto-focusing and is set up to provide the output signal of the sensor 211 to the focus calculating section 215. White blood cell detection is performed by the white blood cell detection section 214 on the basis of an output signal in accordance with the incident light of the sensor 212. Information to be used for an auto-focus operation is calculated by the focus calculating section 215 on the basis of an output signal in accordance with the incident light of the sensor 211. The auto-focus operation is performed on the basis of the information.

In addition, the microscope unit 2 includes a control section 216 and communication interfaces 217 and 218. The control section 216 includes a CPU and a memory, and is connected to the XY stage driving circuit 23, the objective lens driving circuit 24, the cassette transport driving circuit 26, the white blood cell detection section 214, the focus calculating section 215 and the communication interfaces 217 and 218 so as to communicate therewith. When the control section 216 executes a control program stored in the memory, the above-described mechanisms are controlled.

The communication interface 217 is an Ethernet (registered trade name) interface. The communication interface 217 is connected to the image processing unit 3 via a communication cable so as to perform data communication therewith. In addition, the communication interface 218 is connected to the CCD camera 213 via an A/D converter 213a and is connected to the image processing unit 3 via a communication cable. An image signal (analog signal) output from the CCD camera 213 is A/D converted by the A/D converter 213a and image data (digital data) output from the A/D converter 213a is provided to the communication interface 218 to be transmitted to the image processing unit 3.

Moreover, the microscope unit 2 includes a two-dimensional bar-code reader 219. A two-dimensional bar-code indicating a specimen ID is printed on a frost section of the slide glass 5 and the two-dimensional bar-code of the slide glass 5 introduced into the microscope unit 2 is read by the two-dimensional bar-code reader 219. In this manner, the read specimen ID is provided to the control section 216.

<Configuration of Image Processing Unit 3>

Figure 3:
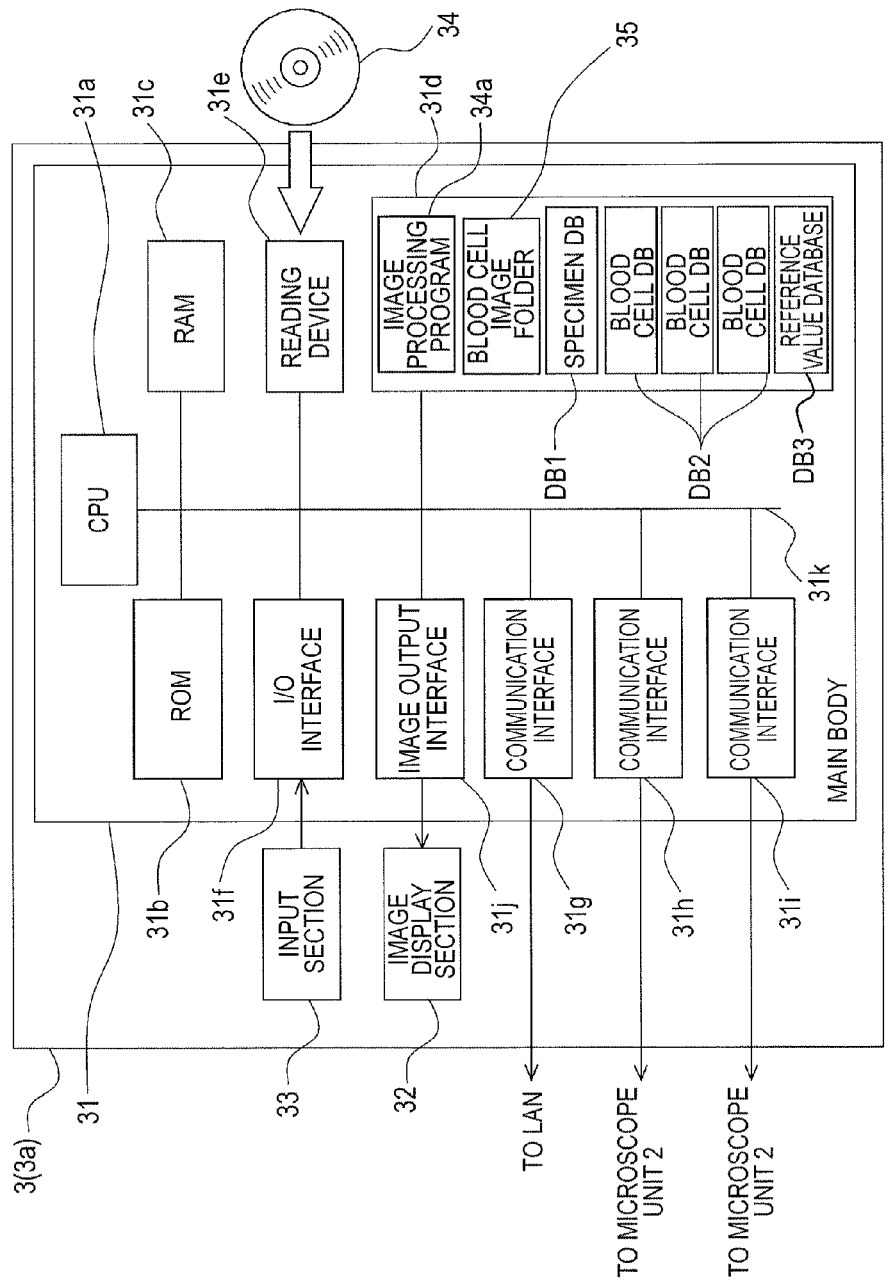
FIG. 3 is a block diagram showing the configuration of an image processing unit according to the embodiment.

Next, the configuration of the image processing unit 3 will be described. FIG. 3 is a block diagram showing the configuration of the image processing unit 3. The image processing unit 3 is realized by a computer 3a. As shown in FIG. 3, the computer 3a includes a main body 31, an image display section 32 and an input section 33. The main body 31 includes a CPU 31a, a ROM 31b, a RAM 31c, a hard disk 31d, a reading device 31e, an I/O interface 31f, a communication interface 31g and an image output interface 31j. The CPU 31a, the ROM 31b, the RAM 31c, the hard disk 31d, the reading device 31e, the I/O interface 31f, the communication interface 31g, a communication interface 31h, a communication interface 31i and the image output interface 31j are connected by a bus 31k.

The CPU 31a can execute a computer program loaded to the RAM 31c. The CPU 31a executes an image processing program 34a to be described later, so that the computer 3a functions as the image processing unit 3.

The ROM 31*b* is composed of a mask ROM, a PROM, an EPROM an EEPROM or the like, and the computer program which is executed by the CPU 31*a* and data used for the computer program are recorded therein.

The RAM 31*c* is composed of a SRAM, a DRAM or the like. The RAM 31*c* is used to read the image processing program 34*a* recorded in the hard disk 31*d*. Moreover, the RAM is used as an operating area of the CPU 31*a* when the CPU 31*a* executes a computer program.

In the hard disk 31*d*, various computer programs for execution by the CPU 31*a*, such as an operating system and an application program, and data which are used to execute the computer programs are installed. The image processing program 34*a* to be described later is also installed in the hard disk 31*d*.

The hard disk 31*d* is provided with a blood cell image folder 35 for storing blood cell images. In the blood cell image folder 35, a folder is provided for each specimen and blood cell images obtained as described later are stored in the folder. The folder provided for each specimen has a folder name including a specimen ID, and the corresponding folder can be specified by the specimen ID. The blood cell image folder 35 is set up so as to share data with the blood cell image display unit 4 and the blood cell image display unit 4 can access files stored in the blood cell image folder 35.

Figure 4A:
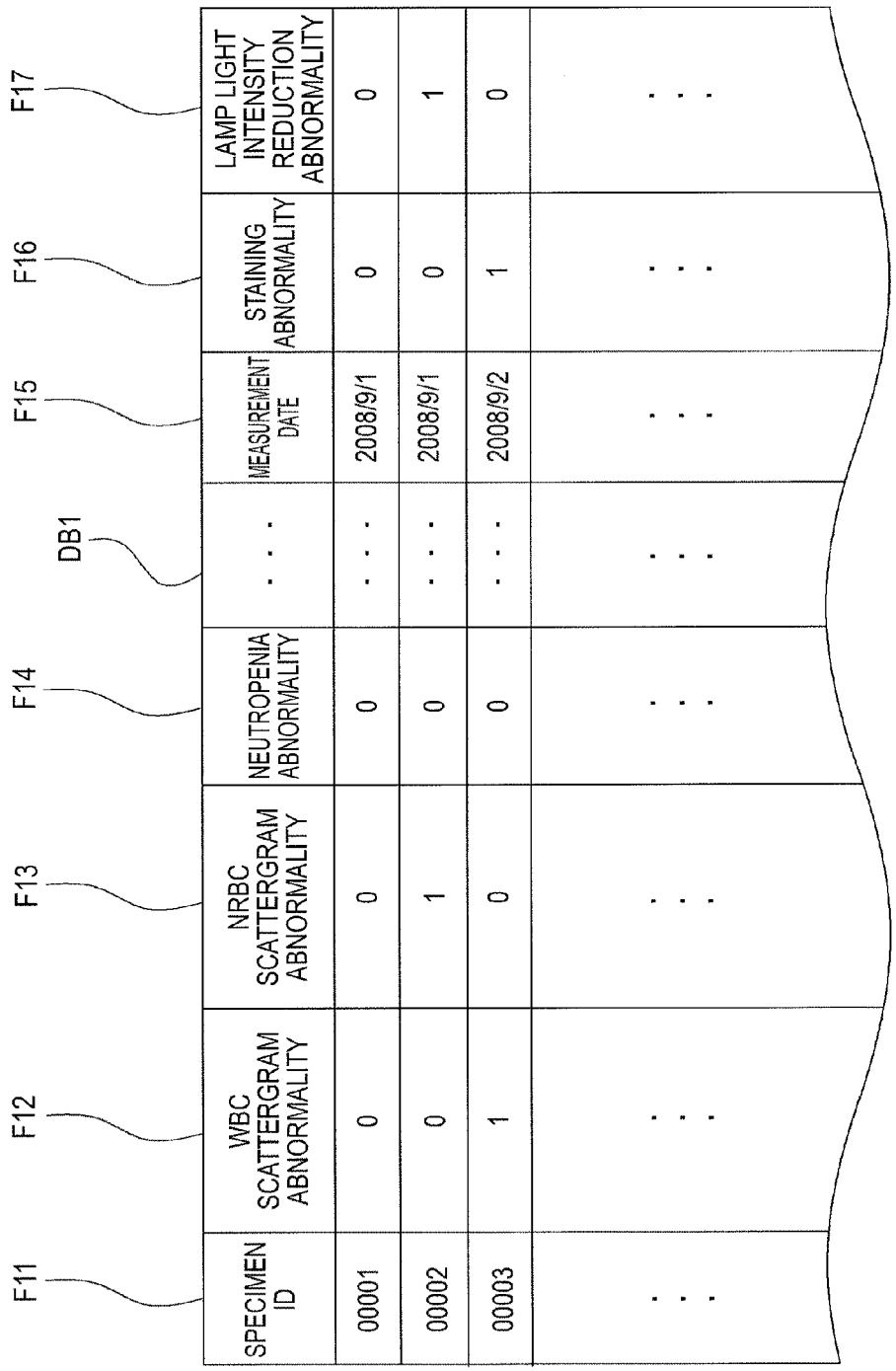
FIG. 4A is a schematic diagram showing the configuration of a specimen database according to the embodiment.

Further, the hard disk 31*d* is provided with a specimen database DB1 for storing information relating to specimens, and a blood cell database DB2 for storing results of the classification of white blood cells by image processing. FIG. 4A is a schematic diagram showing the configuration of the specimen database DB1 and FIG. 4B is a schematic diagram showing the configuration of the blood cell database DB2. The specimen database DB1 includes a specimen field F11 for storing specimen IDs, fields F12, F13, F14 . . . for storing various information on results that are determined to be abnormal as a result of the analysis of the multiple automatic blood cell analyzing apparatus (not shown), such as information (white blood cell scattergram abnormality flag) showing whether a white blood cell scattergram abnormality is confirmed, information (NRBC scattergram abnormality flag) showing whether an NRBC (nucleated red blood cell) scattergram abnormality is confirmed and information (neutropenia abnormality flag) showing whether a neutropenia abnormality is confirmed. The specimen database DB1 also includes a field F15 for storing dates of measurements performed by the sample imaging apparatus 1, a staining abnormality field F16 for storing information (staining abnormality flag) showing whether a staining abnormality has occurred, and a light intensity abnormality field F17 for storing information (lamp light intensity abnormality flag) showing whether a lamp light intensity abnormality has occurred. In the fields storing the information showing abnormalities, such as the white blood cell scattergram abnormality field F12, the NRBC scattergram abnormality field F13, the neutropenia abnormality field F14, the staining abnormality field F16 and the light intensity abnormality field F17, "0" is stored when an abnormality has not occurred, and "1" is stored when an abnormality has occurred. Although omitted for the simplicity of the drawing, the specimen database DB1 is provided with a field for storing the numerical data of the analysis results (the number of white blood cells, the number of red blood cells, et al.) from the multiple automatic blood cell analyzing apparatus. Moreover, the specimen database DB1 is also provided with a field for storing patients' names, a field for storing information specifying a hospital ward, a field for storing ages, a field for storing a number N of white blood cells counted by the microscope unit 2, and the like.

The blood cell database DB2 is provided for each specimen and each blood cell database DB2 includes data indicating a specimen ID. By this, the blood cell database DB2 corresponding to the specimen ID can be specified. The blood cell database DB2 is provided with a white blood cell ID field F21 for storing white blood cell IDs specifying the white blood cells, a type field F22 for storing classification results of the white blood cells and a reconfirmation object field F23 for storing information for specifying the white blood cells which cannot be classified. In the reconfirmation object field F23, "0" is stored when the white blood cell classification is normally performed, and "1" is stored when the classification cannot be performed and the white blood cells becomes an object for reconfirmation.

A reference value database DB3 stores a reference value TB which is used to detect lamp light intensity abnormalities and reference values TN1 and TN2 which are used to detect staining abnormalities in a blood smear.

The reading device 31*e* is composed of a flexible disk drive, a CD-ROM drive, a DVD-ROM drive or the like and can read the computer program or data recorded in a portable recording medium 34. In the portable recording medium 34, the image processing program 34*a* is stored which prompts the computer to function as the image processing unit 3. The computer 3*a* can read the image processing program 34*a* from the portable recording medium 34 and install the image processing program 34*a* in the hard disk 31*d*.

The image processing program 34*a* is not only provided by the portable recording medium 34 and can be also provided from an external device, which is connected to the computer 3*a* by an electric communication line (which may be wired or wireless) to communicate therewith via the electric communication line. For example, the image processing program 34*a* is stored in the hard disk of a server computer on the internet and the computer 3*a* accesses the server computer to download the computer program and install the computer program in the hard disk 31*d*.

Furthermore, in the hard disk 31*d*, for example, a multitasking operating system is installed such as Windows (registered trade name) which is made and distributed by Microsoft Corporation in America. In the following description, the image processing program 34*a* according to this embodiment operates on the above operating system.

The I/O interface 31*f* is composed of, for example, a serial interface such as USB, IEEE1394 or RS-232C, a parallel interface such as SCSI, IDE or IEEE1284, and an analog interface including a D/A converter and an A/D converter. The input section 33 is composed of a keyboard and a mouse and is connected to the I/O interface 31*f*, and the user uses the input section 33 to input data to the computer 3*a*. The CCD camera 213 provided in the microscope unit 2 is connected to the I/O interface 31*f* to take images obtained by an imaging operation of the CCD camera 213.

The communication interfaces 31*g* and 31*h* are Ethernet (registered trade name) interfaces. The communication interface 31*g* is connected to the blood cell image display unit 4 via a LAN. By using the communication interface 31*g*, the computer 3*a* can send and receive data between the blood cell image display unit 4 connected to the LAN and a host computer (not shown) by using a predetermined communication protocol. The communication interface 31*h* is connected to the communication interface 217 of the microscope unit 2 via a communication cable to perform data communication therewith.

The communication interface 31i is connected to the communication interface 218 of the microscope unit 2 via a communication cable to perform data communication therewith. Accordingly, images captured by the CCD camera 213 are received by the communication interface 31i.

The image output interface 31i is connected to the image display section 32 composed of a LCD or a CRT to output a picture signal corresponding to the image data provided from the CPU 31a to the image display section 32. The image display section 32 displays an image (screen) in accordance with an input picture signal.

<Configuration of Blood Cell Image Display Unit 4>

The blood cell image display unit 4 is configured from a computer. The blood cell image display unit 4 is connected to the image processing unit 3 via a LAN to read and display blood cell images in the blood cell image folder 35 provided in the hard disk 31d of the image processing unit 3.

Figure 5:
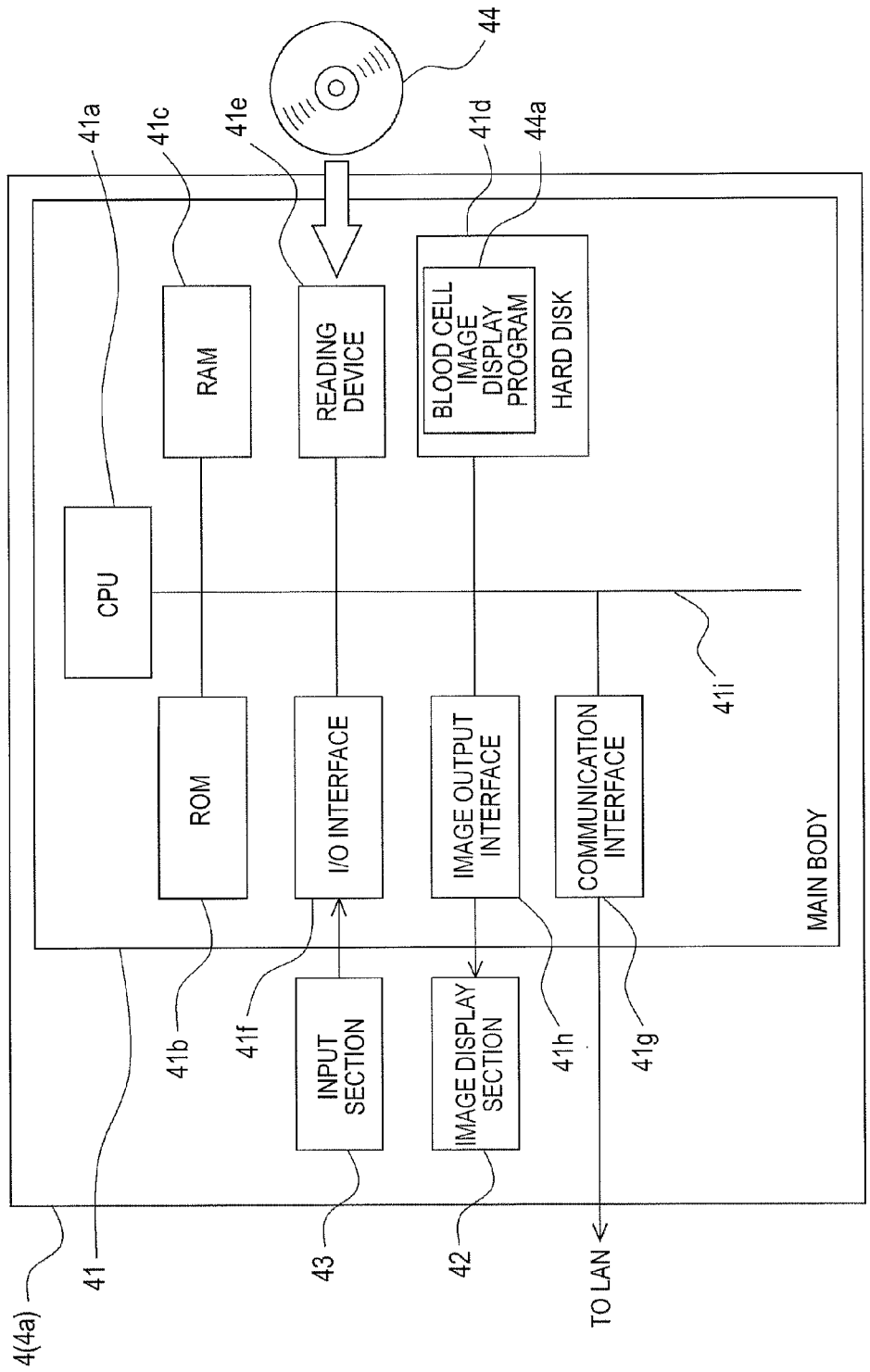
FIG. 5 is a block diagram showing the configuration of a blood cell image display unit according to the embodiment.

FIG. 5 is a block diagram showing the configuration of a blood cell image display unit 4. The blood cell image display unit 4 is realized by a computer 4a. As shown in FIG. 5, the computer 4a includes a main body 41, an image display section 42 and an input section 43. The main body 41 includes a CPU 41a, a ROM 41b, a RAM 41c, a hard disk 41d, a reading device 41e, an I/O interface 41f, a communication interface 41g and an image output interface 41h. The CPU 41a, the ROM 41b, the RAM 41c, the hard disk 41d, the reading device 41e, the I/O interface 41f, the communication interface 41g, and the image output interface 41h are connected by a bus 41i.

In the hard disk 41d, various computer programs for being executed by the CPU 41a, such as an operating system and an application program, and data which are used to execute the computer programs are installed. A blood cell image display program 44a to be described later is also installed in the hard disk 41d.

The reading device 41e is composed of a flexible disk drive, a CD-ROM drive, a DVD-ROM drive or the like and can read the computer program or data recorded in a portable recording medium 44. In the portable recording medium 44, the blood cell image display program 44a is stored which prompts the computer to function as the blood cell image display unit 4. The computer 4a can read the blood cell image display program 44a from the portable recording medium 44 and install the blood cell image display program 44a in the hard disk 41d.

The I/O interface 41f is composed of, for example, a serial interface such as USB, IEEE1394, SAS, SATA or RS-232C, a parallel interface such as SCSI, IDE or IEEE1284, and an analog interface including a D/A converter and an A/D converter. The input section 43 composed of a keyboard and a mouse is connected to the I/O interface 41f and the user uses the input section 43 to input data to the computer 4a.

The communication interface 41g is an Ethernet (registered trade name) interface. The communication interface 41g is connected to the image processing unit 3 via a LAN. Thanks to the communication interface 41g, the computer 4a can send and receive data between the image processing unit 3 connected to the LAN and a host computer (not shown) by using a predetermined communication protocol.

Since the other configurations of the blood cell image display unit 4 are the same as the configurations of the above-described image processing unit 3, a description thereof will be omitted.

[Operation of Sample Imaging Apparatus]

Next, an operation of the sample imaging apparatus 1 according to this embodiment will be described.

<Blood Cell Image Registration Operation>

First, a blood cell image registration operation of imaging blood cells by the sample imaging apparatus 1 and storing the blood cell image will be described. Before the operation of the sample imaging apparatus 1, a blood smear is prepared. The blood smear preparing apparatus disposed near the sample imaging apparatus 1 prepares a blood smear by aspirating a specimen contained in a blood collection tube, dropping and spreading the specimen on a slide glass, and dipping the slide glass in a stain solution. The staining which is performed on a sample by the blood smear preparing apparatus is May-Grunward-Giemsa staining (May-Giemsa staining), Wright-Giemsa staining or simple Wright staining. The blood smear (slide glass 5) prepared in this manner is automatically supplied to the microscope unit 2 from the blood smear preparing apparatus.

Figure 6:
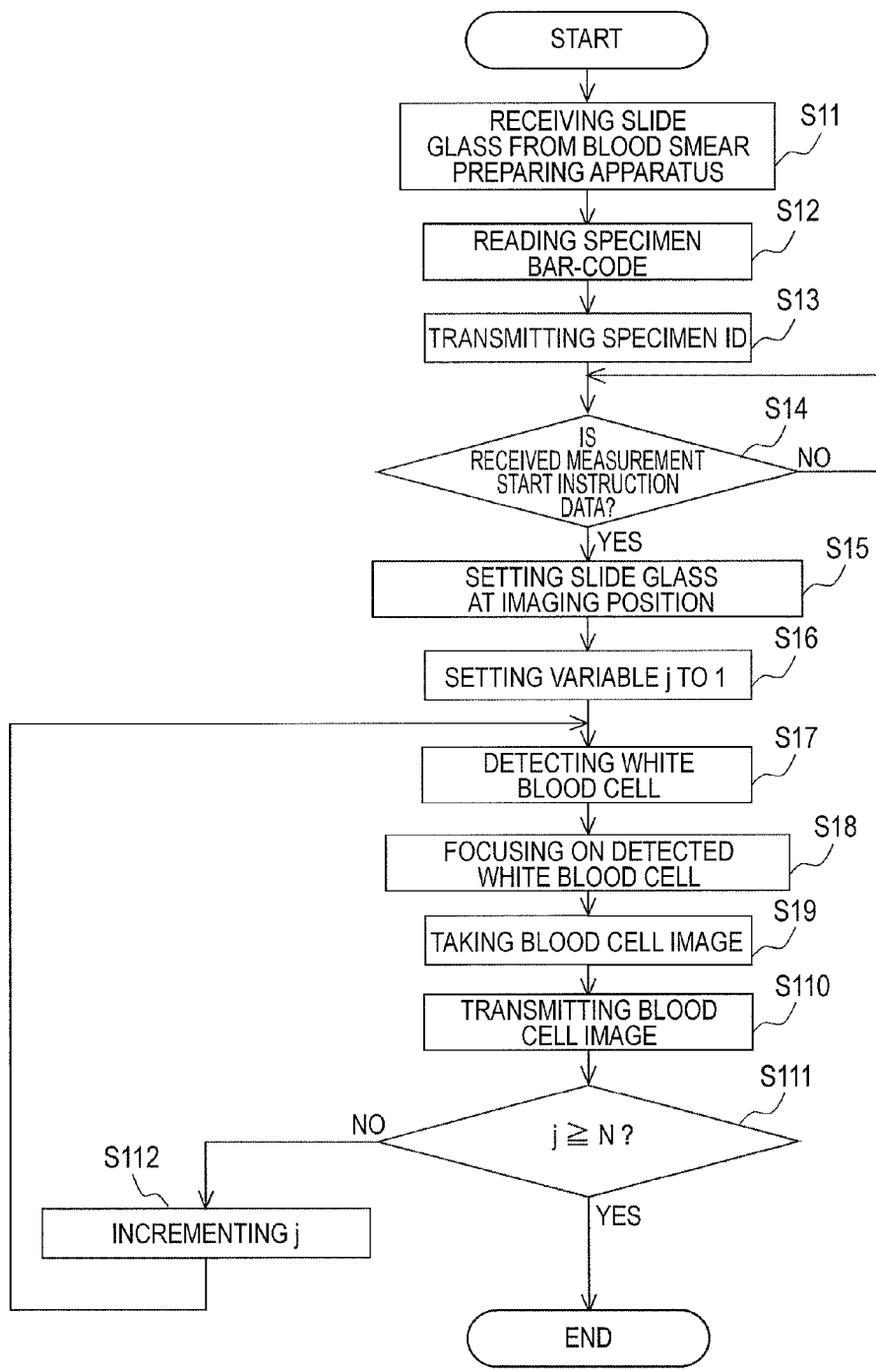
FIG. 6 is a flowchart showing the procedure of an operation of the microscope unit in a blood cell image registration operation.
Figure 7A:
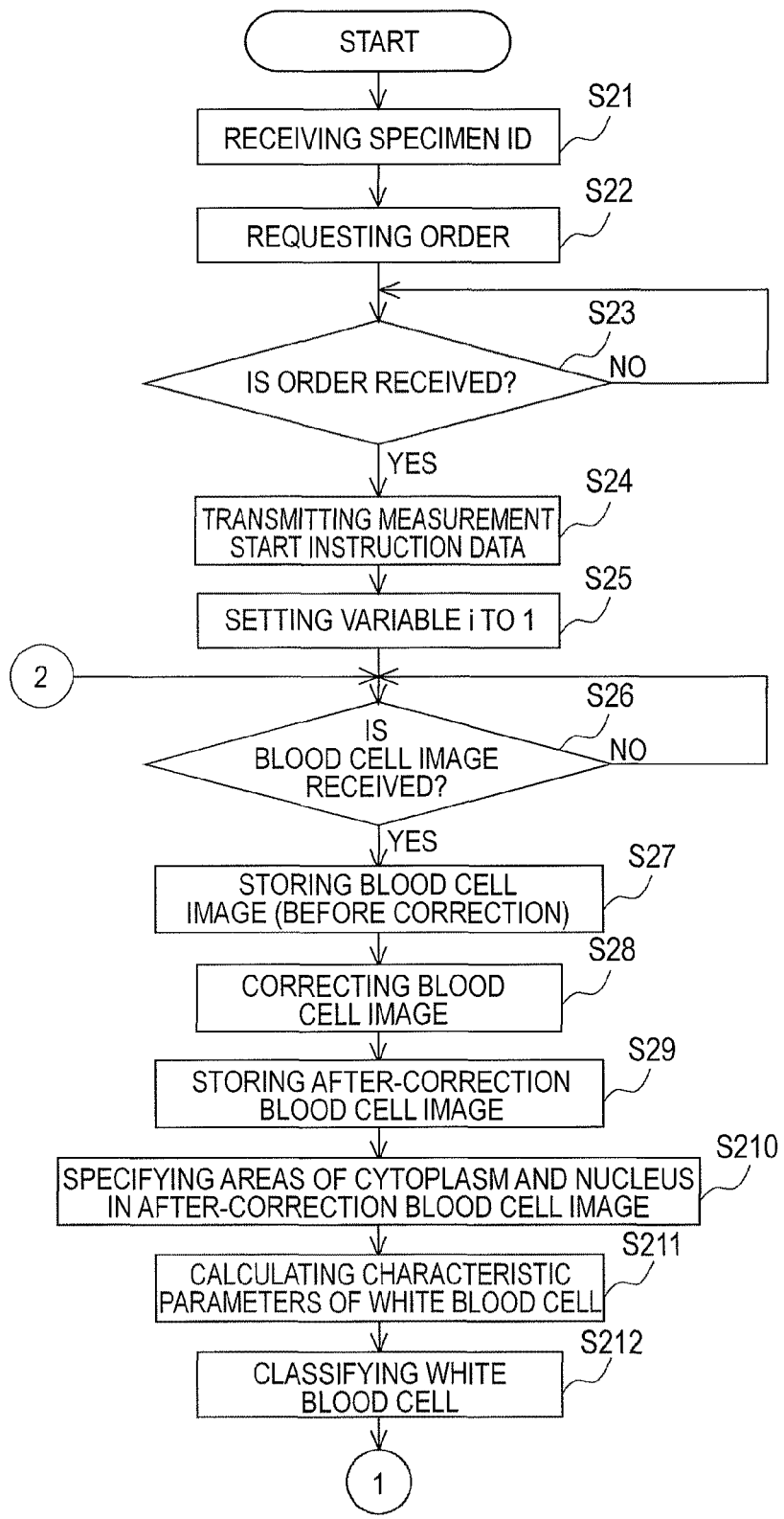
FIG. 7A is a flowchart (first half) showing the procedure of an operation of the image processing unit in the blood cell image registration operation.

FIG. 6 is a flowchart showing the procedure of an operation of the microscope unit 2 in the blood cell image registration operation, and FIGS. 7A and 7B are flowcharts showing the procedure of an operation of the image processing unit 3 in the blood cell image registration operation. When receiving the slide glass 5 from the blood smear preparing apparatus, the microscope unit 2 detects the slide glass via a sensor (not shown) (Step S11). A control program which is executed by the control section 216 is an event-driven program, and in the control section 216 of the microscope unit 2, a process of Step S12 is invoked when an event occurs in which the slide glass 5 is received from the blood smear preparing apparatus.

In Step S12, the control section 216 transports the slide cassette 25 accommodating the received slide glass 5 to a predetermined bar-code reading position and the specimen bar-code is read by the two-dimensional bar-code reader 219 (Step S12). Next, the control section 216 transmits the specimen ID obtained in Step S12 to the image processing unit 3 via the communication interface 217 (Step S13).

The specimen ID transmitted from the microscope unit 2 is received by the communication interface 31h of the image processing unit 3 (Step S21 of FIG. 7A). The image processing program 34a which is executed by the CPU 31a of the image processing unit 3 is an event-driven program, and in the CPU 31a, a process of Step S22 is invoked when an event occurs in which the specimen ID is received.

In Step S22, the CPU 31a transmits order request data including the received specimen ID to a host computer via the communication interface 31g (Step S22). The order transmitted from the host computer includes the specimen ID, the patient's name, the patient's sex, hospital ward information, comments, analysis results of the multiple automatic blood cell analyzing apparatus (numerical data such as the number of white blood cells and the number of red blood cells), various abnormality information (white blood cell scattergram abnormality flag, NRBC scattergram abnormality flag, neutropenia abnormality flag, neutrophilia abnormality flag, monocytosis abnormality flag, eosinophilia abnormality flag, basophilic leukocytosis abnormality flag, leukopenia abnormality flag, leukocytosis abnormality flag, erythroblastosis abnormality flag, etc.) detected by the multiple automatic blood cell analyzing apparatus, and the number N of white blood cells counted. The CPU 31a stands by to receive the order (No in Step S23). When the order is received (Yes in Step S23), the CPU 31a transmits measurement start instruction data, which includes the number N of white blood cells counted by the microscope unit 2 and included in the order, to the microscope unit 2 via the communication interface 31h (Step S24), and sets a variable i indicating the number of blood cell images analyzed to 1 (Step S25).

Herein, the microscope unit 2 stands by to receive the measurement start instruction data (No in Step S14 of FIG. 6). When the measurement start instruction data transmitted from the image processing unit 3 is received by the communication interface 217 of the microscope unit 2 (Yes in Step S14), the control section 216 transports the slide cassette 25 to a predetermined position to hold the slide glass 5 which has been stopped at the predetermined position by the chuck section 27. Then, by retracting the chuck section 27, the slide glass is drawn from the slide cassette 25 and is set at a predetermined position (imaging position) in the XY stage 21 (Step S15). In addition, the control section 216 sets a variable j indicating the number of imaging operations to 1 (Step S16).

Figure 8:
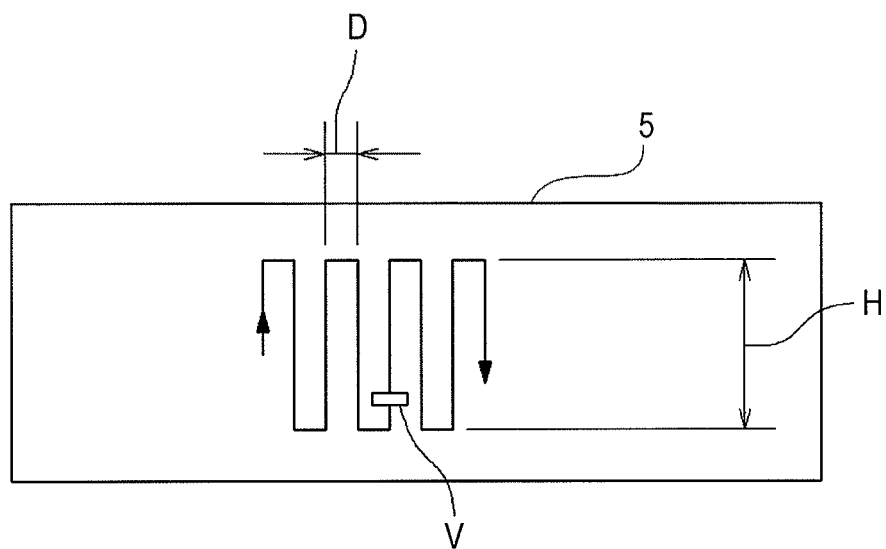
FIG. 8 is a diagram explaining a pattern of scanning of a specimen on a slide glass in white blood cell detection.

Next, the white blood cell in the blood applied to the slide glass 5 is detected (Step S17). The above detection is performed using the sensor 212. The sensor 212 is a line sensor and has a field of view of about 400 µm. FIG. 8 is a diagram explaining a pattern of the scanning of the specimen on the slide glass in the white blood cell detection. The control section 216 moves the XY stage 21 in the X and Y directions so that the sensor 212 performs a scan operation on the slide glass 5 in a substantially zigzag manner from one end toward the other end in the longitudinal direction (see FIG. 8 for reference). Generally, an interval D in the longitudinal direction of the slide glass 5 of the substantial zigzag scanning is set in the range of about 300 to 500 µm due to the viewpoint of the prevention of detection failures and the increase of scanning efficiency. A dimension H in the width direction of the slide glass 5 being scanned is set in the range of about 14 to 18 mm because the width of the slide glass 5 is normally about 26 mm.

Figure 9A:
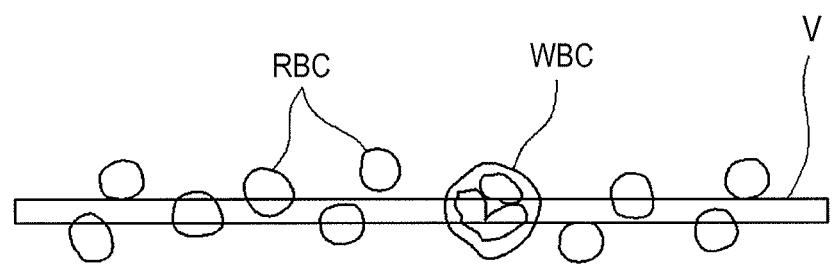
FIG. 9A is a diagram explaining a field of view of a line sensor for detecting a white blood cell.
Figure 9B:
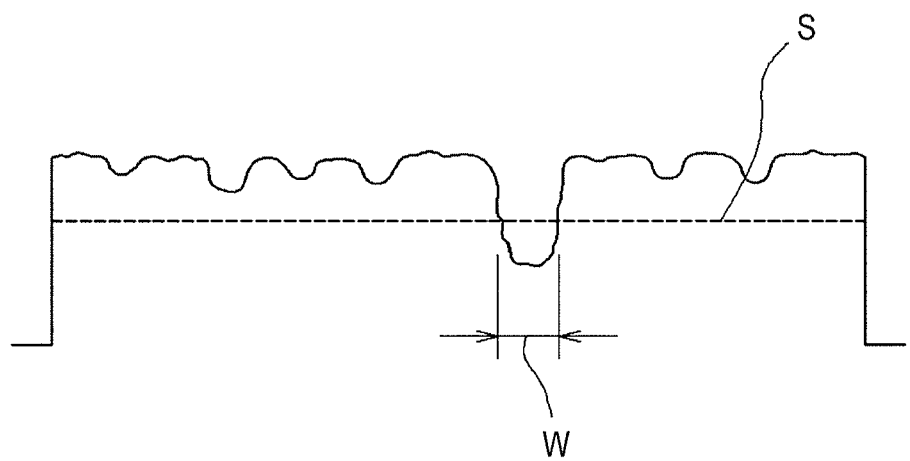
FIG. 9B is a diagram showing a signal waveform of the line sensor for detecting a white blood cell.

Red blood cells do not absorb much red color component of light, but the nucleus of a white blood cell does absorb a large amount of the red color component of light. Accordingly, by detecting the red color component, the white blood cell and the red blood cell can be easily distinguished. FIG. 9A is a diagram explaining the field of view of the line sensor 212, and FIG. 9B is a diagram showing a signal waveform of the line sensor 212. FIG. 9A shows that a white blood cell WBC is present in a field of view V of the line sensor 212. In this case, as shown in FIG. 9B, the red color component of a signal detected by the line sensor 212 has a value equal to or less than a reference value S in a part in which the white blood cell WBC is present. Using this phenomenon, the white blood cell can be detected in the blood. By detecting the width W of the portion in which the red color component of the signal has a value equal to or less than the reference value S, it is checked whether the portion emitting the signal is the nucleus of the white blood cell.

Next, the control section 216 performs an auto-focus operation (Step S18). As shown in FIG. 2, the direction of the light passing through the slide glass 5 and the objective lens 22 is changed by a prism mirror 29a, and the light is divided into light which is directed to the CCD camera 213 and light which is directed to the sensors 211 and 212 by the half mirrors 29. The line sensor 211 for auto-focusing is composed of two line sensors 211a and 211b.

As shown in FIG. 2, the line sensor 211a which is one of the two line sensors 211a and 211b for auto-focusing is disposed in front of (close to the objective lens on the optical path) a focus position (a position which is in focus), and the other line sensor 211b is disposed behind (far from the objective lens on the optical path) the focus position. In addition, the position of the objective lens is adjusted on the basis of a value which is obtained by the integral of the difference between the output signals of the two line sensors, so that the focus of the objective lens is on the specimen on the slide glass.

Next, the control section 216 instructs the communication interface 218 to take and transmit the image of the CCD camera 213. Thus, the image of the white blood cell detected in Step S17 is taken (Step S19) and the blood cell image is transmitted to the image processing unit 3 (Step S110). After that, the control section 216 determines whether the required counted number of the white blood cells has been satisfied, that is, whether j is equal to or greater than N (Step S111). When j is less than N (No in Step S111), the control section increments j by 1 (Step S112) and returns the process to Step S17 to repeat the detection of the white blood cells. On the other hand, when j is equal to or greater than N in Step S111 (Yes in Step S111), the control section 216 completes the process.

After the above Step S25, the CPU 31a stands by to receive the blood cell image (No in Step S26 of FIG. 7A). When the blood cell image transmitted from the microscope unit 2 is received by the communication interface 31h of the image processing unit 3 (Yes in Step S26), the CPU 31a stores the received blood cell image in the hard disk 31d (Step S27). In the process of Step S27, a white blood cell ID corresponding to the received blood cell image is generated, and the blood cell image is stored as image data with a file name including the white blood cell ID. Then, the CPU 31a performs a correction process on the blood cell image (Step S28). In such a correction process, the luminance values of RGB components of all the pixels of the blood cell image are subjected to a linear correction so that an average luminance value of the background portion (portion other than the blood cells) of the blood cell image reaches a predetermined value (for example, 225). In the hard disk 31d, the blood cell image after the correction is stored separately from the blood cell image before the correction (Step S29). The blood cell image after the correction also has a file name (a file name different from that of the blood cell image before the correction) which includes the white blood cell ID.

Figure 10A:
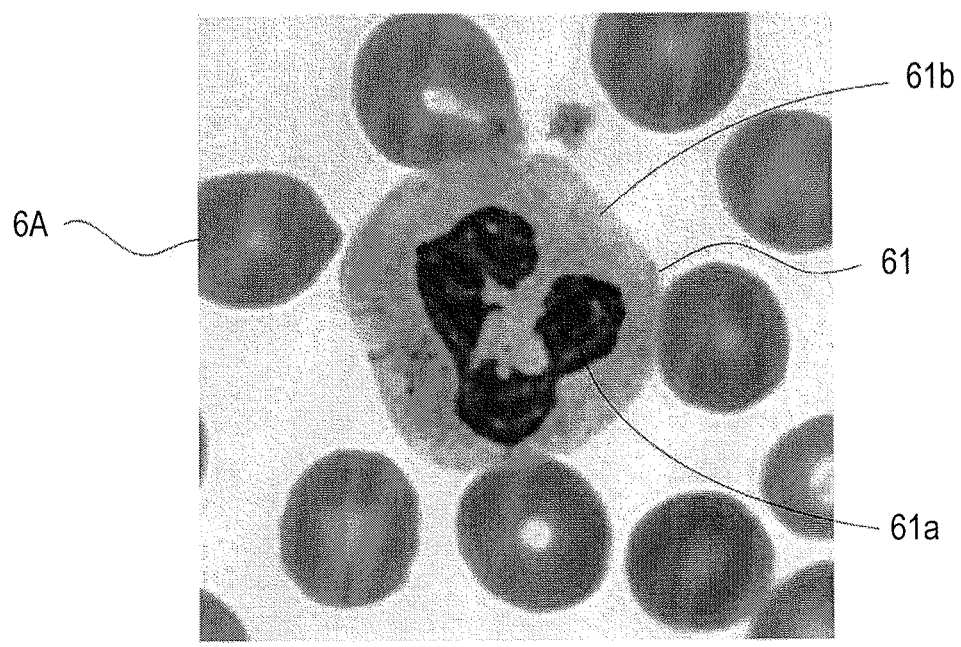
FIG. 10A is a diagram showing an example of an after-correction blood cell image when the staining is normally performed.

Next, the CPU 31a specifies areas of cytoplasm and a nucleus in the after-correction blood cell image (Step S210). FIG. 10A is a diagram showing an example of an after-correction blood cell image. As shown in FIG. 10A, in an after-correction blood cell image 6A, a white blood cell image 61 is included. In a stained white blood cell, a nucleus has a color different from that of a cytoplasm. Moreover, the colors of the cytoplasm and the nucleus of the white blood cell are different from color of a red blood cell and a background. Accordingly, in the process of Step S210, a nucleus area 61a and a cytoplasm area 61b which are included in the white blood cell image 61 are specified by using a RGB value of the white blood cell image 61.

Next, the CPU 31a calculates various characteristic parameters of the white blood cell on the basis of the after-correction blood cell image (Step S211). The characteristic parameters include the area of a white blood cell's nucleus, the number of nuclei, irregularity, tone and concentration (unevenness) of a white blood cell's nucleus, the area, tone and concentration (unevenness) of a white blood cell's cytoplasm, and the area ratio and the concentration ratio between the nucleus and the cytoplasm, which can be obtained on the basis of color signals (G, B, R) of the image.

Next, using the obtained characteristic parameters, the CPU 31a classifies the type of the white blood cell (Step S212). Specifically, for example, several characteristic parameters of the white blood cell are sequentially compared with judgment criteria values, which are determined for the parameters in advance, to gradually narrow down the type of the white blood cell. In this manner, the imaged white blood cell is classified as a mature white blood cell such as a lymphocyte, a monocyte, an eosinophil, a basophil or a neutrophil (bacillary, lobulated), as an immature white blood cell such as a blast cell, a young granulocyte or an atypical lymphocyte, or as an erythroblast.

As described above, in the sample imaging apparatus 1 according to this embodiment, the classification of the white blood cell is performed using the color information of the blood cell image. Accordingly, when a staining abnormality occurs in a blood smear, a blood cell image is obtained which includes a white blood cell image having a color different from that in the case in which the staining is normally performed. In addition, when the light intensity of the lamp is reduced, the background portion which is unaffected by the staining is corrected by the above correction process to have a certain luminance value, and thus a blood cell image is obtained which includes a white blood cell image having a color different from that in the case in which the light intensity of the lamp is normal.

Figure 10B:
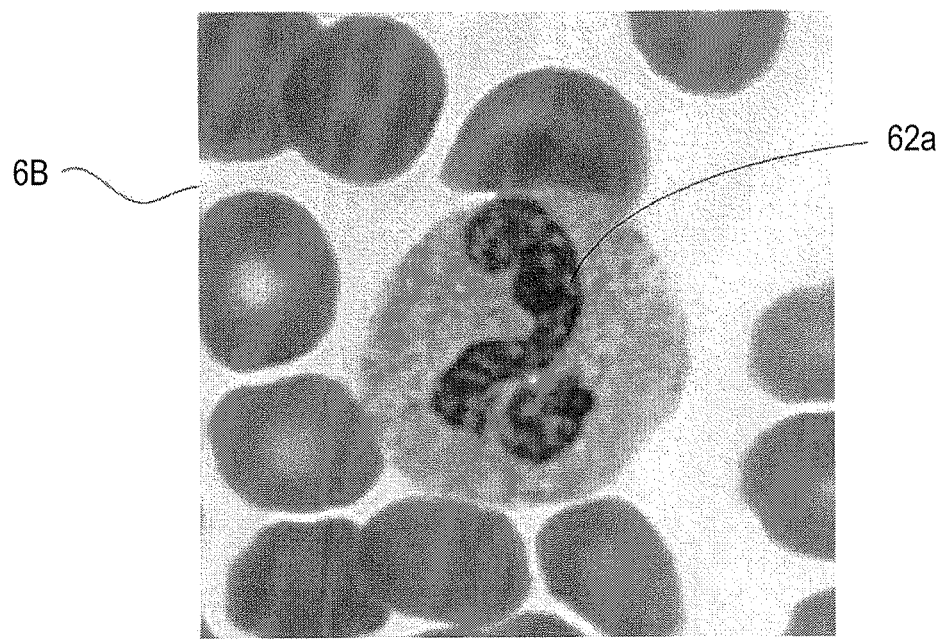
FIG. 10B is a diagram showing an example of an after-correction blood cell image when a staining abnormality occurs.

This will be described using the drawings. FIG. 10A is a diagram showing an example of an after-correction blood cell image when the staining is normally performed and FIG. 10B is a diagram showing an example of an after-correction blood cell image when a staining abnormality occurs. When May-Giemsa staining, Wright-Giemsa staining and simple Wright staining are performed, in a blood cell image 6A which is obtained when the staining is normally performed and a blood cell image 6B which is obtained when a staining abnormality occurs, colors of nucleus areas are particularly different from each other. A nucleus area 62a of the blood cell image 6B which is obtained when the staining abnormality occurs has a color lighter than that of a nucleus area 61a of the blood cell image 6 which is obtained when the staining is normally performed. Further, although not shown in the FIGS. 10A and 10B, due to over-staining, the color of a nucleus area may be darker than that of a nucleus area which is obtained when the staining is normally performed, and thus the classification may not be normally performed. Accordingly, when a luminance value of a certain color component (green component in this embodiment) of the nucleus area 61a is not in a normal range, it can be determined that a staining abnormality has occurred.

Figure 11A:
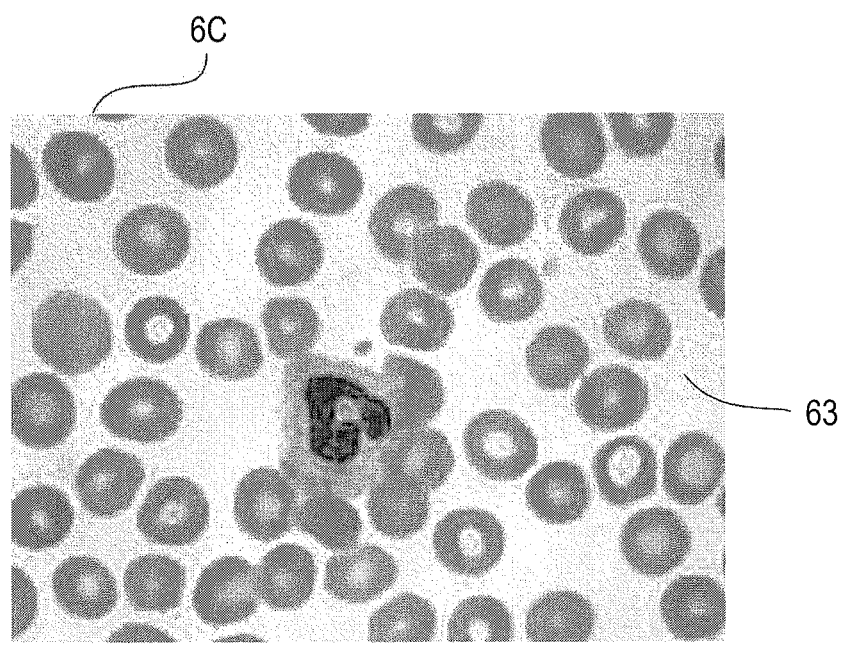
FIG. 11A is a diagram showing an example of a before-correction blood cell image which is obtained by an imaging operation at normal lamp light intensity.
Figure 11B:
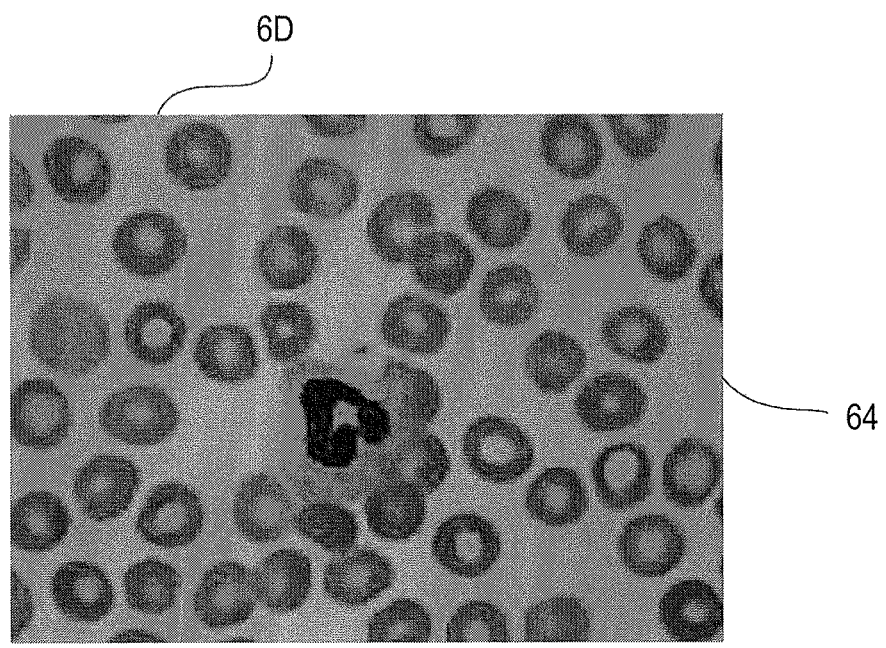
FIG. 11B is a diagram showing an example of a before-correction blood cell image which is obtained by an imaging operation when lamp light intensity is reduced.

FIG. 11A is a diagram showing an example of a before-correction blood cell image which is obtained by an imaging operation at a normal lamp light intensity and FIG. 11B is a diagram showing an example of a before-correction blood cell image which is obtained by an imaging operation when the lamp light intensity is reduced. In a before-correction blood cell image 6C which is obtained when a lamp light intensity is normal and a before-correction blood cell image 6D which is obtained when a lamp light intensity abnormality occurs, luminance of background areas are particularly different. The background area is unaffected by the influence of the staining, but is affected by the light intensity of the lamp. The luminance of a background area 64 of the blood cell image 6D which is obtained when a lamp light intensity abnormality occurs is lower than the luminance of a background area 63 of the blood cell image 6C which is obtained when a lamp light intensity abnormality does not occur. Accordingly, when a luminance value of a certain color component (green component in this embodiment) of the background area of the before-correction blood cell image is lower than a reference value, it can be determined that the lamp light intensity abnormality has occurred.

In this embodiment, in order to detect a staining abnormality and a lamp light intensity abnormality, the image processing unit 3 performs the following process. First, the CPU 31a obtains G values (luminance value of green component) of pixels in a background area of a before-correction blood cell image, that is, an area other than a blood cell area in a before-correction blood cell image, calculates an average value of the obtained G values, and stores the obtained value (hereinafter, referred to as "background G value") in the RAM 31c (Step S213).

Next, the CPU 31a determines whether a white blood cell in the blood cell image is classified as a neutrophil as a result of the classification in Step S212 (Step S214). When the white blood cell is classified as a neutrophil (Yes in Step S214), the CPU obtains the G values of the pixels in an area of a white blood cell's nucleus in the after-correction blood cell image, calculates an average value of the obtained G values, and stores the obtained value (hereinafter, referred to as "nucleus G value") in the RAM 31c (Step S215). Then, the CPU 31a performs a process of Step S216.

On the other hand, in Step S214, when the white blood cell in the blood cell image is not classified as a neutrophil (No in Step S214), the CPU 31a performs the process of Step S216.

In Step S216, the CPU 31a determines whether the required counted number of the white blood cells has been satisfied, that is, whether i is equal to or greater than N (Step S216). When i is less than N (No in Step S216), the CPU increments i by 1 (Step S217), returns the process to Step S26, and stands by to receive another blood cell image.

On the other hand, when i is equal to or greater than N in Step S216 (Yes in Step S216), the CPU 31a calculates an average value BA (hereinafter, referred to as "average background G value") of the G values of the background stored in the RAM 31c (Step S218) and an average value NA (hereinafter, referred to as "average nucleus G value") of the G values of the nucleus stored in the RAM 31c (Step S219).

Next, the CPU 31a determines whether the average background G value BA is larger than a predetermined reference value TB (Step S220). When the average background G value BA is equal to or smaller than the reference value TB (No in Step S220), the CPU sets the lamp light intensity abnormality flag provided in the RAM 31c to 1 (Step S221), performs a process of displaying on the image display sections 32 and 42 an error screen for notifying the image display section 32 of the generation of the lamp light intensity abnormality (Step S222), and performs a process of Step S224.

Figure 12A:
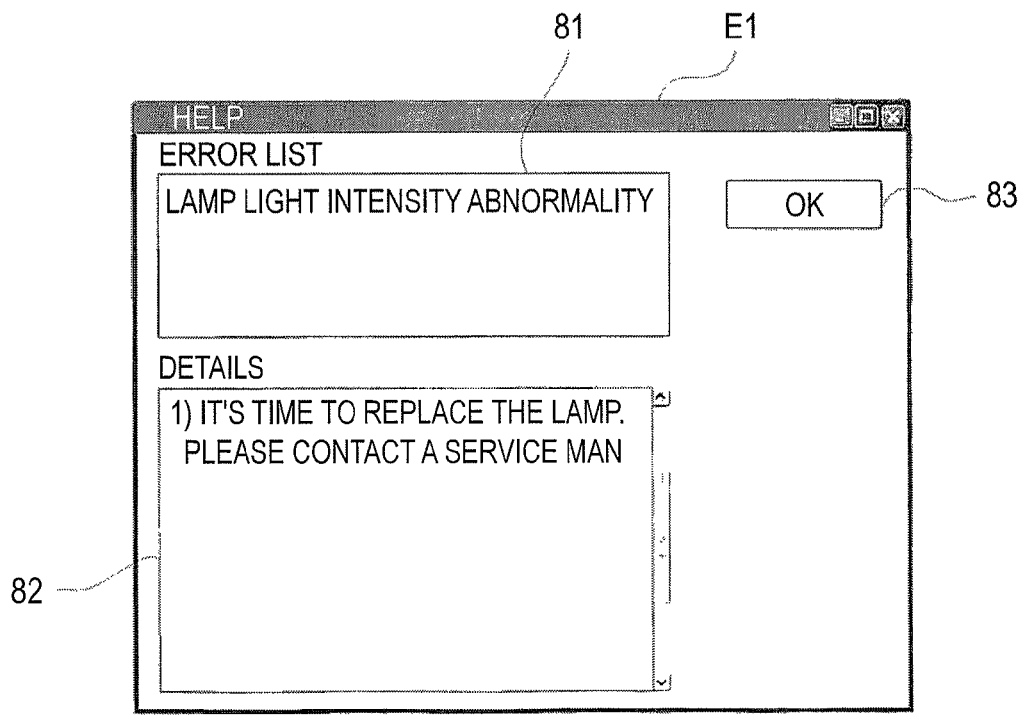
FIG. 12A is a diagram showing an error screen for notifying the generation of lamp light intensity abnormality.

FIG. 12A is a diagram showing the error screen for notifying the generation of the lamp light intensity abnormality. When a lamp light intensity abnormality occurs, an error screen E1 is displayed as shown in FIG. 12A. The error screen E1 includes an error list display area 81 for displaying error information, a detailed information display area 82 for displaying detailed information for coping with the error and an OK button 83 which is used to close the screen. In the help screen E1 when a lamp light intensity abnormality occurs, "abnormality due to lamp light intensity insufficiency" is displayed in the error list display area 81 and the message "1) It's time to replace the lamp. Please contact a service man." is displayed in the detailed information display area 82.

On the other hand, when the average background G value BA is larger than the reference value TB (Yes in Step S220), the CPU 31a sets the lamp light intensity abnormality flag to 0 (Step S223) and performs the process of Step S224.

In Step S224, the CPU 31a determines whether the average nucleus G value NA is larger than a predetermined lower-limit reference value TN1 and smaller than a predetermined upper-limit reference value TN2 (Step S224). When the average nucleus G value NA is equal to or smaller than the lower-limit reference value TN1, or equal to or larger than the upper-limit reference value TN2 (No in Step S224), the CPU sets the staining abnormality flag provided in the RAM 31c to 1 (Step S225), performs a process of displaying on the image display sections 32 and 42 an error screen for notifying the image display section 32 of the generation of a staining abnormality (Step S226), and performs a process of Step S228.

Figure 12B:
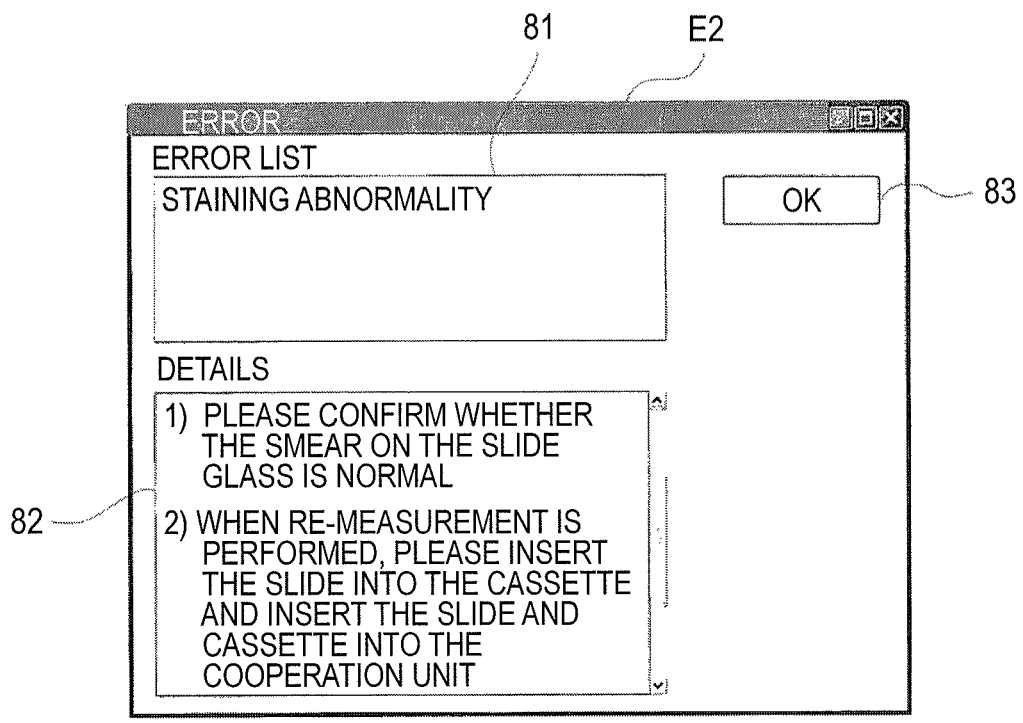
FIG. 12B is a diagram showing an error screen for notifying the generation of a staining abnormality.

FIG. 12B is a diagram showing the error screen for notifying the generation of a staining abnormality. When the staining abnormality occurs, an error screen E2 is displayed as shown in FIG. 12B. Like the error screen E1, the error screen E2 includes an error list display area 81 for displaying error information, a detailed information display area 82 for displaying detailed information for coping with the error and an OK button 83 which is used to close the screen. When the staining abnormality occurs, "staining abnormality" is displayed in the error list display area 81 and the messages "1) Please confirm whether the smear on the slide is normal." and "2) When re-measurement is performed, please insert the slide into the cassette and insert the slide and cassette into the cooperation unit." is displayed in the detailed information display area 82.

The display of the above-described error screens E1 and E2 is completed when a user operates the input section 43 to select the OK button 83.

On the other hand, when the average nucleus G value NA is larger than the lower-limit reference value TN1 and smaller than the upper-limit reference value TN2 (Yes in Step S224), the CPU 31a sets the staining abnormality flag to 0 (Step S227) and performs the process of Step S228.

In Step S228, the CPU 31a registers the information relating to the specimen and the classification result obtained as described above in the specimen database DB1 and the blood cell database DB2 of the hard disk 31d (Step S228) and completes the process.

<Operation of Displaying Blood Cell Image>

Figure 13A:
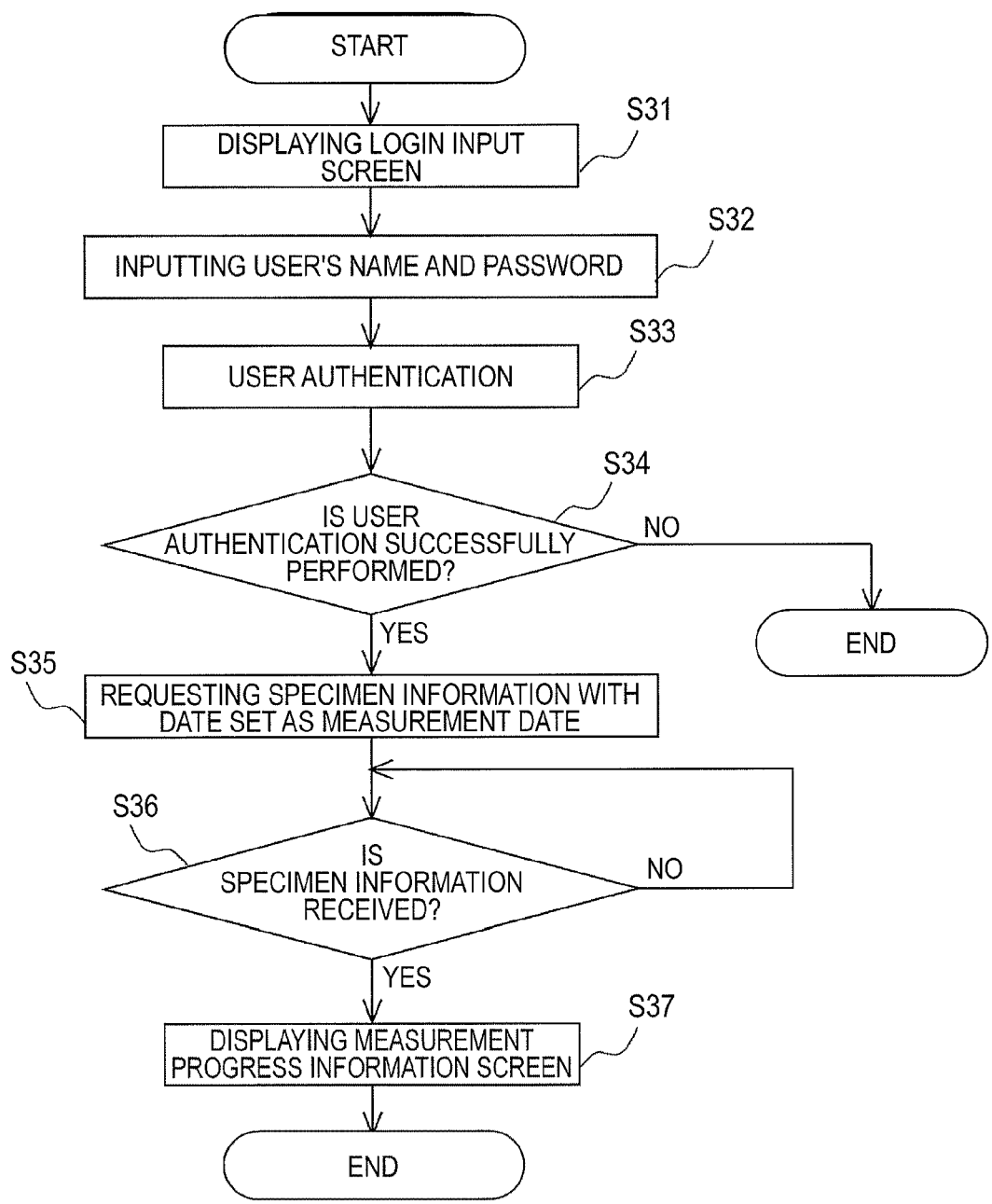
FIG. 13A is a flowchart showing the procedure of an initialization operation of the blood cell image display unit in a blood cell image display operation.
Figure 13B:
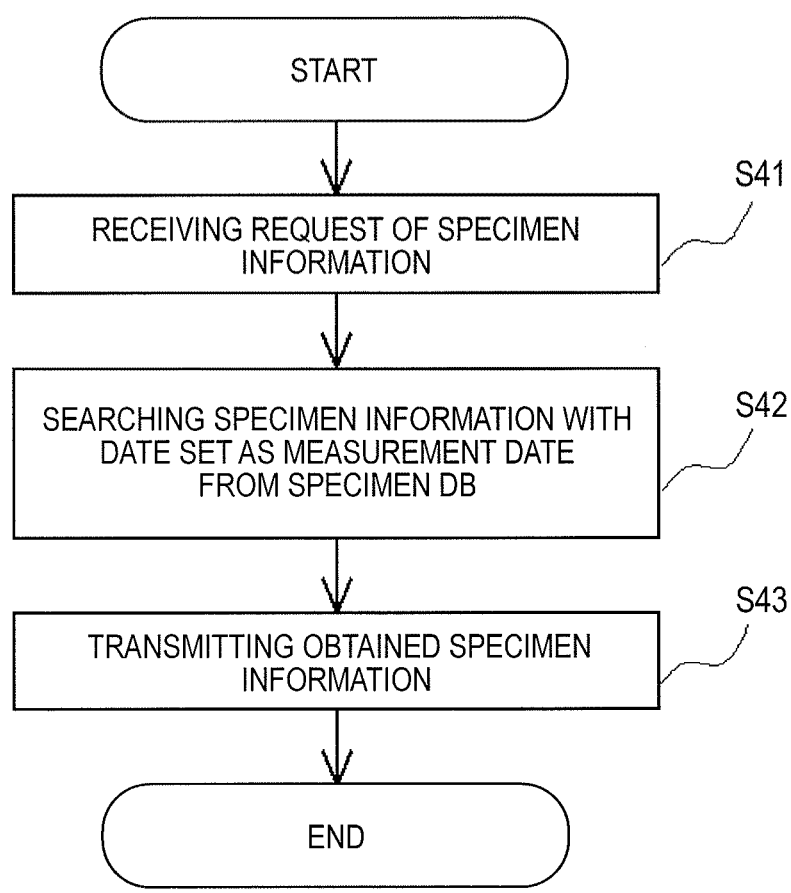
FIG. 13B is a flowchart showing the procedure of a specimen information transmitting operation of the image processing unit in the blood cell image display operation.

FIG. 13A is a flowchart showing the procedure of an initialization operation of the blood cell image display unit 4 in a blood cell image display operation, and FIG. 13B is a flowchart showing the procedure of a specimen information transmitting operation of the image processing unit 3 in the blood cell image display operation. The user operates the input section 43 of the computer 4a to instruct the execution of the blood cell image display program 44a. The CPU 41a of the computer 4a receives the instruction and executes the blood cell image display program 44a. In this manner, the computer 4a functions as the blood cell image display unit 4.

Immediately after the initiation of the blood cell image display program 44a, a login input screen prompting the input of a user's name and a password is displayed (Step S31 of FIG. 13A). The user input the user's name and the password in the login input screen (Step S32). The blood cell image display program 44a, which is executed by the CPU 41a of the blood cell image display unit 4, is an event-driven program, and in the CPU 41a, a process of Step S33 is invoked when an event occurs in which the user's name and the password are input.

In Step S33, the CPU 41a performs a user authentication process. When the user authentication fails (No in Step S34), the CPU 41a completes the process. When the user is successfully authenticated by using the login process (Yes in Step S34), the CPU 41a transmits request data of specimen information with the date set as the measurement date to the image processing unit 3 via the communication interface 41g (Step S35).

The request data transmitted from the blood cell image display unit 4 is received by the communication interface 31h of the image processing unit 3 (Step S41 of FIG. 13B). In the CPU 31a, a process of Step S42 is invoked when an event occurs in which the request data is received.

In Step S42, from the specimen database DB1, the CPU 31a obtains the specimen information with the date set as the measurement date (Step S42). Next, the CPU 31a transmits the obtained specimen information to the blood cell image display unit 4 via the communication interface 31g (Step S43) and completes the process.

After transmitting the request data of specimen information, the CPU 41a of the blood cell image display unit 4 stands by to receive the specimen information (No in Step S36 of FIG. 13A). When the specimen information transmitted from the image processing unit 3 is received by the communication interface 41g of the blood cell image display unit 4 (Yes in Step S36), a measurement progress screen (not shown) is displayed (Step S37) and the process is completed. In the measurement progress screen, the specimen information relating to plural specimens is displayed as a list. The specimen information list is provided with "staining abnormality" and "lamp light intensity abnormality" areas. A mark indicating the generation of a staining abnormality is displayed in a staining abnormality area of a specimen in which the staining abnormality is detected, and a mark indicating the generation of a lamp light intensity abnormality is displayed in a lamp light intensity abnormality area of a specimen in which the lamp light intensity abnormality is detected. Moreover, in the measurement progress screen, the user can select one of the specimen information displayed as a list. By selecting one specimen information and subsequently performing a predetermined operation (for example, the double-clicking of the left button of a mouse), it is possible to provide an instruction for displaying a blood cell image relating to the specimen.

Figure 14A:
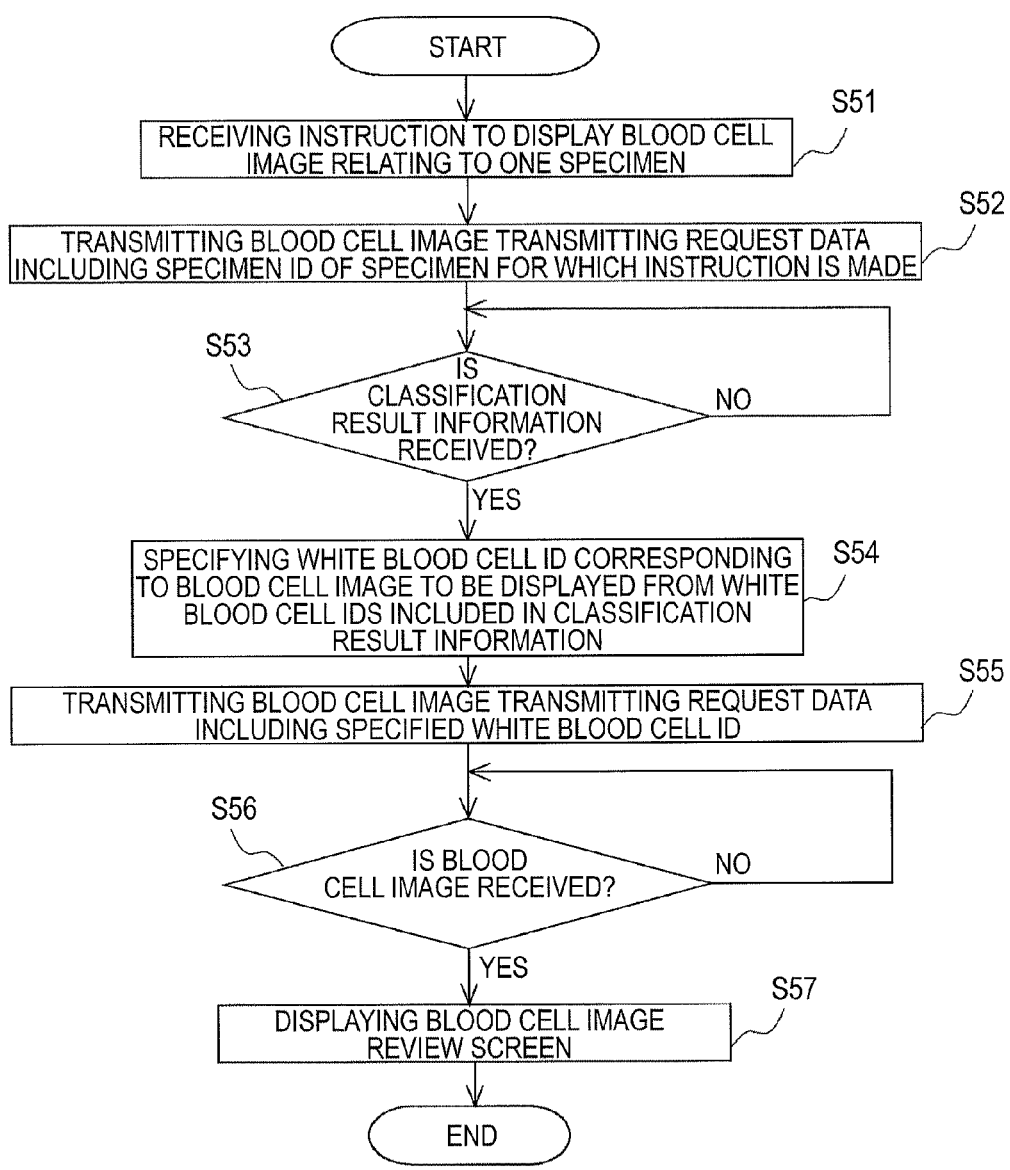
FIG. 14A is a flowchart showing the procedure of an image display operation of the blood cell image display unit in the blood cell image display operation.
Figure 14B:
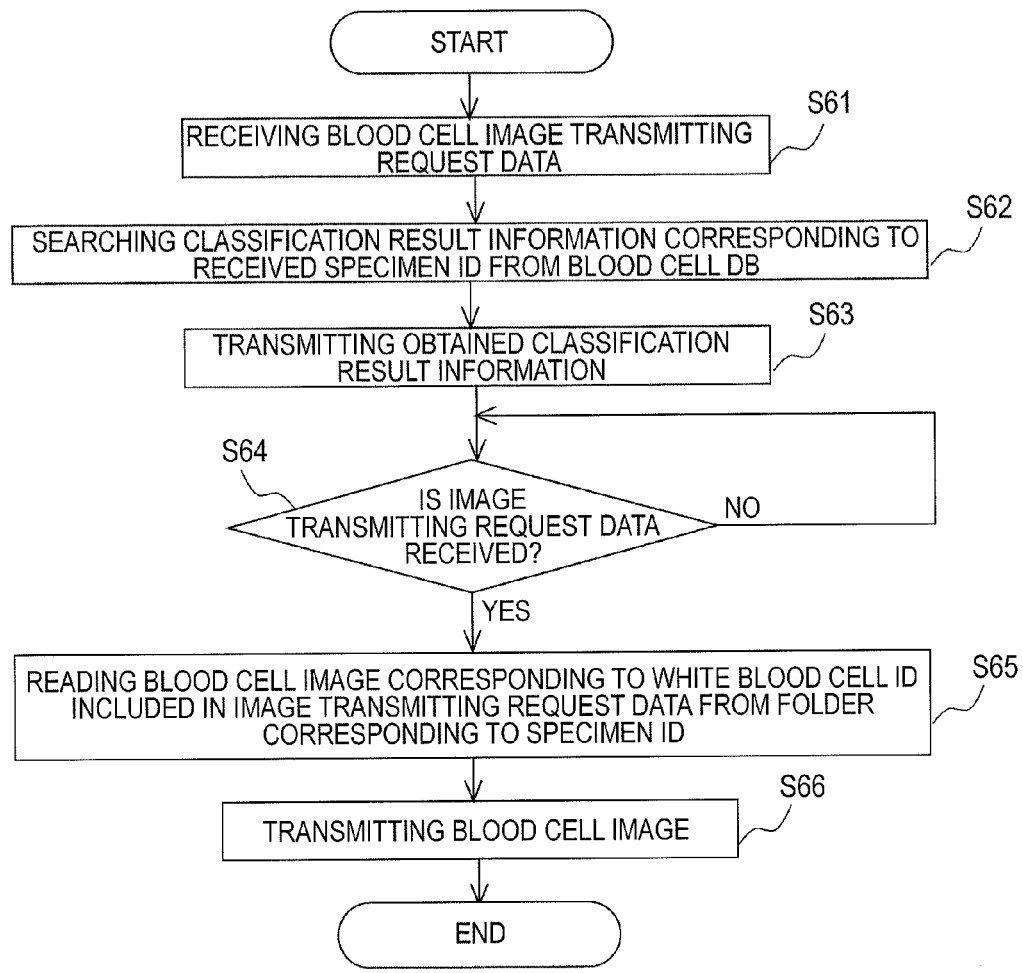
FIG. 14B is a flowchart showing the procedure of a blood cell image transmitting operation of the image processing unit in the blood cell image display operation.

FIG. 14A is a flowchart showing the procedure of an image display operation of the blood cell image display unit 4 in the blood cell image display operation, and FIG. 14B is a flowchart showing the procedure of a blood cell image transmitting operation of the image processing unit 3 in the blood cell image display operation. In the blood cell image display unit 4, when an event occurs, in which the instruction for displaying the blood cell image relating to one specimen is received as described above, in a state in which the measurement progress screen is displayed (Step S51), a process of Step S52 is invoked.

In Step S52, the CPU 41a transmits blood cell image transmitting request data, including the specimen ID of the specimen for which the instruction is made, to the image processing unit 3 via the communication interface 41g (Step S52).

The request data transmitted from the blood cell image display unit 4 is received by the communication interface 31h of the image processing unit 3 (Step S61 of FIG. 14B). In the CPU 31a, a process of Step S62 is invoked when an event occurs in which the request data is received.

In Step S62, the CPU 31a obtains classification result information from the blood cell database DB2 corresponding to the specimen ID (Step S62). The classification result information includes white blood cell IDs specifying the white blood cells, the types (monocyte, neutrophil, basophil, eosinophil, lymphocyte, et al.) as the result of the white blood cell classification, and information indicating whether the classification can be performed. In addition, in the classification result information, the type information or classification failure information of the white blood cell corresponds to the white blood cell ID. That is, from the white blood cell ID, the classification result information can specify the type of the white blood cell or whether the classification of the white blood cell had failed.

Next, the CPU 31*a* transmits the obtained classification result information to the blood cell image display unit 4 via the communication interface 31*g* (Step S63).

After transmitting the request data of the classification result information, the CPU 41*a* of the blood cell image display unit 4 stands by to receive the classification result information (No in Step S53 of FIG. 14A). When the classification result information transmitted from the image processing unit 3 is received by the communication interface 41*g* of the blood cell image display unit 4 (Yes in Step S53), in accordance with, for example, a display condition for displaying only an image of a certain type of a white blood cell, a white blood cell ID corresponding to the blood cell image to be displayed is specified from the white blood cell IDs included in the classification result information (Step S54), and the image transmitting request data including the specified white blood cell ID is transmitted to the image processing unit 3 via the communication interface 41*g* (Step S55). In Step S54, one or more white blood cell IDs are specified and the image transmitting request data includes all the specified white blood cell IDs.

After transmitting the classification result information, the CPU 31*a* of the image processing unit 3 stands by to receive the image transmitting request data (No in Step S64 of FIG. 14B). When the request data transmitted from the blood cell image display unit 4 is received by the communication interface 31*h* of the image processing unit 3 (Yes in Step S64), the CPU 31*a* reads the blood cell image (after-correction blood cell image) corresponding to the white blood cell ID included in the image transmitting request data from the folder corresponding to the specimen ID in the blood cell image folder 35 in the hard disk 31*d* (Step S65), transmits the read blood cell image to the blood cell image display unit 4 via the communication interface 31*g* (Step S66), and completes the process.

After transmitting the image transmitting request data, the CPU 41*a* of the blood cell image display unit 4 stands by to receive the blood cell image (No in Step S56 of FIG. 14A). When the blood cell image transmitted from the image processing unit 3 is received by the communication interface 41*g* of the blood cell image display unit 4 (Yes in Step S56), a blood cell image review screen is displayed (Step S57) and the process is completed.

Figure 15:
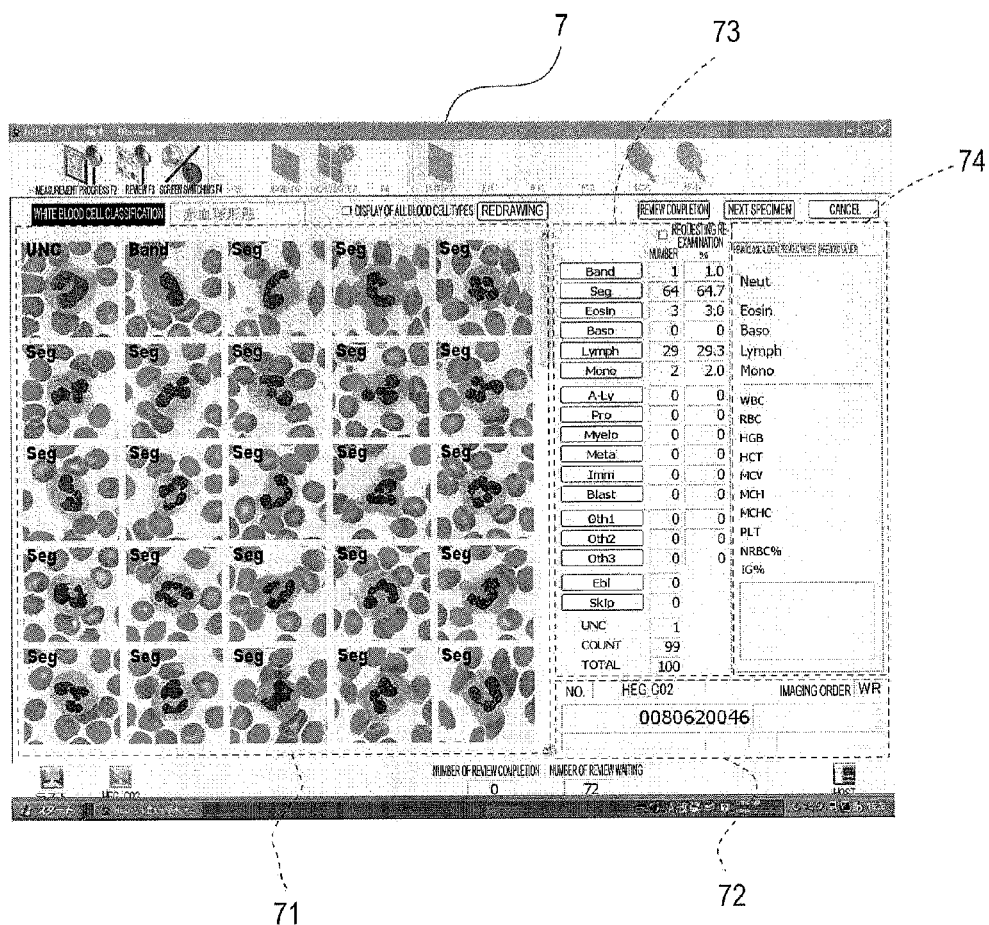
FIG. 15 is a diagram showing an example of a blood cell image review screen.

FIG. 15 is a diagram showing an example of the blood cell image review screen. In a blood cell image review screen 7, a blood cell image display area 71 for displaying one or more blood cell images, a patient information display area 72 for displaying patient information, a counted value display area 73 for displaying the result of the counting of each type of classified blood cells, and an analysis result display area 74 for displaying the analysis result of the multiple automatic blood cell analyzing apparatus are included. In the blood cell image display area, images which are obtained by reducing received blood cell images are displayed as a list. A blood cell type is displayed with a string of characters ("MONO" for a monocyte, "NEUT" for a neutrophil, "EO" for an eosinophil, "BASO" for a basophil, "LYMP" for a lymphocyte, etc.) in each reduced image.

With the above-described configuration, a staining abnormality in the slide glass 5 can be detected, and when the blood cell classification is poorly performed due to the staining abnormality, it is possible to specify that the cause of the poor classification is the staining abnormality. In addition, in the sample imaging apparatus according to this embodiment, an abnormality in the light intensity of the lamp which is used for imaging can be detected, and when the blood cell classification is poorly performed due to the lamp light intensity abnormality, it is possible to specify that the cause of the poor classification is the lamp light intensity abnormality. The lamp for imaging is a consumable part which deteriorates with the passage of time, so the light intensity thereof is gradually reduced, or the lamp may suddenly not emit light. Accordingly, the user can replace the lamp in a timely basis by detecting the lamp light intensity abnormality.

In the blood cell image of the white blood cell, the G values (nucleus G value) of the pixels of the nucleus area indicate the characteristic of the white blood cell. A blood cell image of a normally stained white blood cell and a blood cell image of a white blood cell with a staining abnormality have different nucleus G values. Accordingly, the staining abnormality can be accurately detected by using the nucleus G value.

The white blood cell includes a nucleus, and the nucleus of the white blood cell is mainly stained in May-Giemsa staining, Wright-Giemsa staining and simple Wright staining. Accordingly, a staining abnormality can be accurately detected by detecting the white blood cell, obtaining a blood cell image of the detected white blood cell, and using the blood cell image of the white blood cell in which there is a large influence due to the staining to detect the staining abnormality.

There are a monocyte, a neutrophil, an eosinophil, a basophil and a lymphocyte as types of white blood cells. White blood cells of different types have different nucleus forms and states of the stained nuclei are also different from each other. Accordingly, a staining abnormality can be accurately detected by detecting the staining abnormality on the basis of a blood cell image of a certain type of a white blood cell (neutrophil).

In the sample imaging apparatus 1 according to this embodiment, the staining abnormality is detected by using the blood cell image of a neutrophil. The number of neutrophils is the largest among white blood cells included in the blood of a normal individual. Accordingly, by using the blood cell image of the neutrophil, the staining abnormality can be detected more stably than in the case in which an image of another type of blood cell is used.

In the sample imaging apparatus 1 according to this embodiment, a nucleus area of the white blood cell is identified from the blood cell image and a staining abnormality is detected on the basis of the nucleus area. As described above, the nucleus of the white blood cell is mainly stained in May-Giemsa staining, Wright-Giemsa staining and simple Wright staining. Accordingly, a staining abnormality can be accurately detected by detecting the staining abnormality on the basis of the nucleus G value obtained from the nucleus area in the blood cell image.

In the sample imaging apparatus 1 according to this embodiment, the nucleus G value as a characteristic value is obtained from plural pixels of the nucleus area of the blood cell image and a staining abnormality is detected on the basis of the nucleus G values of the plural blood cell images. The nucleus G value of the plural pixels included in the nucleus area may be substantially higher or lower than that of other pixels. Accordingly, a staining abnormality can be accurately and stably detected by using the plural nucleus G values as described above.

In the sample imaging apparatus 1 according to this embodiment, a staining abnormality is detected on the basis of an average value of the obtained plural nucleus G values. When the nucleus G values of the white blood cells in the same specimen follow a regular distribution, the average value is used and thus it can be used as a value in which there is relatively little change and indicates the characteristic of a population (nucleus G values of the white blood cells in the same specimen).

In the sample imaging apparatus 1 according to this embodiment, an abnormality in the light intensity of the lamp which is used for imaging is detected on the basis of a background area of the blood cell image. The influence of the staining on the background area of the blood cell image is small, and when the lamp emits light at a constant light intensity, the background areas in the plural blood cell images are maintained at the same luminance. Accordingly, the lamp light intensity abnormality can be accurately detected by using the background area (area other than blood cells).

In addition, when a staining abnormality of the slide glass 5 is detected, the user is notified of the generation of the staining abnormality by the above-described help screen. Accordingly, since the user confirms the apparatus state of the blood smear preparing apparatus or the stain solution, it is possible to quickly deal with the abnormality and solve the staining abnormality in an early stage.

Moreover, when a lamp light intensity abnormality is detected, the user is notified of the generation of the lamp light intensity abnormality by the above-described help screen. Accordingly, since the user can replace the lamp or deal with the abnormality by contacting a service man, it is possible to solve the lamp light intensity abnormality in an early stage.

(Other Embodiments)

In the above-described embodiments, the sample imaging apparatus which images a blood smear to obtain a blood cell image has been described. However, the invention is not limited to this. A sample imaging apparatus which images a sample, which is obtained by thinly slicing a tissue collected from a human body, adhering the tissue on a slide glass and staining the tissue with a stain solution, to obtain a cell image which includes a cell also may be employed.

In the above-described embodiments, the configuration has been described in which a staining abnormality of a sample and an abnormality in the light intensity of the lamp which is used for imaging can be detected. However, the invention is not limited to this. A configuration may be employed in which a staining abnormality of a sample can be detected, but a lamp light intensity abnormality cannot be detected, or a configuration also may be employed in which a lamp light intensity abnormality can be detected, but a staining abnormality of a sample cannot be detected.

In the above-described embodiments, the configuration has been described in which when the average nucleus G value NA is larger than the predetermined lower-limit reference value TN1 and smaller than the predetermined upper-limit reference value TN2, a staining abnormality is determined. However, the invention is not limited to this. A configuration also may be employed in which when the upper-limit reference value is not provided and the average nucleus G value NA is equal to or smaller than the lower-limit reference value TN1, a staining abnormality is determined.

In the above-described embodiments, the configuration has been described in which the average nucleus G value which is obtained by averaging the G values of a nucleus area of a blood cell image is used as a characteristic parameter indicating a characteristic of the staining to detect a staining abnormality. However, the invention is not limited to this. A configuration may be employed in which the average nucleus G value is not used, but a value which is obtained by averaging the B values or R values of a nucleus area of a blood cell image is used as a characteristic parameter to detect a staining abnormality, or a configuration may also be employed in which a G value, a B value or a R value of one pixel included in a nucleus area of a blood cell image is used as a characteristic parameter to detect a staining abnormality.

In the above-described embodiments, the configuration has been described in which the average background G value which is obtained by averaging the G values of a background area of a blood cell image is used as a characteristic parameter indicating a characteristic of the lamp light intensity to detect a lamp light intensity abnormality. However, the invention is not limited to this. A configuration may be employed in which the average background G value is not used, but a value which is obtained by averaging the B values or R values of a background area of a blood cell image is used as a characteristic parameter to detect a lamp light intensity abnormality, or a configuration may also be employed in which a G value, a B value or a R value of one pixel included in a background area of a blood cell image is used as a characteristic parameter to detect a lamp light intensity abnormality.

In the above-described embodiments, the configuration has been described in which a blood cell image of a neutrophil is used to detect a staining abnormality. However, the invention is not limited to this. A configuration also may be employed in which the blood cell image of a neutrophil is not used, but a blood cell image of another type of white blood cell such as a monocyte, an eosinophil, a basophil or a lymphocyte is used to detect a staining abnormality. However, the number of neutrophils is the largest among white blood cells included in the blood of a normal individual. Accordingly, by using the blood cell image of the neutrophil, a staining abnormality can be detected more stably than in the case in which an image of another type of blood cell is used. In addition, a configuration also may be employed in which a red blood cell area of a blood cell image is used to detect a staining abnormality since the whole red blood cell is stained with a stain solution.

In the above-described embodiments, the configuration has been described in which by executing the image processing program, the computer functions as the image processing unit 3 to detect a staining abnormality and a lamp light intensity abnormality. However, the invention is not limited to this. A configuration also may be employed in which a staining abnormality and a lamp light intensity abnormality are detected using a dedicated hardware such as FPGA, ASIC or the like capable of executing the same process as the image processing program.

In the above-described embodiments, the configuration has been described in which the blood cell image and the information notifying a staining abnormality or a lamp light intensity abnormality are displayed by the blood cell image display unit 4 which is provided independently of the image processing unit 3. However, the invention is not limited to this. A configuration also may be employed in which by one unit having the function of the image processing unit 3 as well as the function of the blood cell image display unit 4, a staining abnormality and a lamp light intensity abnormality are detected, and the blood cell image and the information notifying the staining abnormality or the lamp light intensity abnormality are displayed.

In the above-described embodiments, the configuration has been described in which the white blood cell classification is performed on the basis of the blood cell image and then a staining abnormality and a lamp light intensity abnormality are detected. However, the invention is not limited to this. A configuration also may be employed in which a staining abnormality and a lamp light intensity abnormality are detected and then the white blood cell classification is performed. In addition, in this case, a configuration may be employed in which the white blood cell classification using the blood cell image is not performed when a staining abnormality or a lamp light intensity abnormality is detected. Accordingly, when it can be assumed that the white blood cell classification cannot be normally performed due to the staining abnormality or the lamp light intensity abnormality, the sample imaging apparatus can be efficiently operated without performing the white blood cell classification.

In the above-described embodiments, the configuration has been described in which a staining abnormality is detected using an after-correction blood cell image. However, the invention is not limited to this. A configuration also may be employed in which a reference value (threshold) is set in accordance with the degree of gain correction of a blood cell image, that is, an amount of the change in the luminance value of each pixel in the blood cell image in the correction and the luminance value of a certain color component (for example, green) of a nucleus area of a before-correction blood cell image is compared with the reference value so as to determine the staining abnormality when the luminance value is equal to or smaller than the reference value. That is, when a correction amount is large, the before-correction blood cell image has a low luminance value in the whole image and thus a low reference value is set; and when a correction amount is small, the before-correction blood cell image has a high luminance value in the whole image and thus a high reference value is set. Accordingly, even using the before-correction blood cell image, it is possible to appropriately detect a staining abnormality.

In the above-described embodiments, the configuration has been described in which all the processes of the image processing program 34a are executed by the single computer 3a. However, the invention is not limited to this. A distribution system also can be employed for distributing the same process as the above-described image processing program 34a to plural apparatuses (computers) and executing the process.

In the above-described embodiments, the configuration has been described in which all the processes of the blood cell image display program 44a are executed by the single computer 4a. However, the invention is not limited to this. A distribution system also can be employed for distributing the same process as the above-described blood cell image display program 44a to plural apparatuses (computers) and executing the process.

What is claimed is:

1. A blood stain sample imaging apparatus that detects improper staining comprising:
   a light source for irradiating a stained blood sample that includes white blood cells having stained nucleuses;
   a white blood cell detector for detecting the white blood cells from the stained blood sample;
   an imaging section for imaging the stained blood sample to generate a plurality of cell images each of which includes at least one of the white blood cells detected by the white blood cell detector; and
   a processor and a memory storing a computer program that configures the processor to perform operations comprising:
   identifying a nucleus area of each the white blood cells based on the cell images;
   classifying the white blood cells into a plurality of types; and
   determining a staining abnormality by:
      determining white blood cell nucleus luminance values of each of the identified nucleus areas;
      generating an average value of the white blood cell nucleus luminance values;
      comparing the average value of the white blood cell nucleus luminance values with a stored acceptable range; and
      outputting an alert indicating a staining abnormality of the stained blood sample to a user of the apparatus in response to a comparison result outside the stored acceptable range.

2. The blood stain sample imaging apparatus of claim 1, wherein each of the white blood cell nucleus luminance values is a luminance value of a specific color component.

3. The blood stain sample imaging apparatus of claim 2, wherein the specific color component is a green component.

4. The blood stain sample imaging apparatus of claim 1, wherein the white blood cell associated with the identified nucleus area for determining the white blood cell nucleus luminance value is a neutrophil.

5. The blood stain sample imaging apparatus of claim 4, wherein the white blood cell nucleus luminance values of each of the identified nucleus area comprise a luminance value of a green component.

6. The blood stain sample imaging apparatus of claim 1, wherein the processor is configured to perform operations further comprising:
   determining a lighting intensity abnormality by:
      determining second luminance values of each of the backgrounds of the cell images;
      generating a second average value of the determined second luminance values;
      comparing the second average value with a stored reference value; and
      outputting an error indication of the lighting intensity abnormality in response to a second comparison result representing the second average value being equal to or smaller than the reference value.

7. The blood stain sample imaging apparatus of claim 6, wherein the processor is configured to perform operations further comprising:
   determining the staining abnormality using the white blood cell nucleus luminance value of a green component; and
   determining the light intensity abnormality of the light source using the second luminance value of the green component.

8. The blood stain sample imaging apparatus of claim 1, wherein
   the white blood cell detector comprises a line sensor configured to detect white blood cells from the stained blood sample irradiated by the light source, and the imaging section comprises a charge-coupled device camera configured to image the detected white blood cell included in the stained blood sample irradiated by the light source.

9. The blood stain sample imaging apparatus of claim 1, comprising an object lens for magnifying the detected white blood cell and line sensors for using auto-focus operation of the object lens.

10. The blood stain sample imaging apparatus of claim 1, comprising a microscope unit configured to magnify the detected white blood cell included in the stained blood sample,
wherein the microscope unit comprises the light source, the white blood cell detector, the imaging section, an object lens for magnifying the detected white blood cell and line sensors for using auto-focus operation of the object lens.

11. The blood stain sample imaging apparatus of claim 1, wherein the computer program configures the processor to perform operations further comprising correcting Red-Green-Blue values of each of the cell images to adjust for a luminance background of the cell images to reach a predetermined value.

12. A blood stain sample imaging apparatus that detects a staining abnormality and a light intensity abnormality, the apparatus comprising:
a light source for irradiating a stained blood sample that includes white blood cells having stained nucleuses;
a white blood cell detector for detecting the white blood cells from the stained blood sample;
an imaging section for imaging the stained blood sample to generate a plurality of cell images each of which includes at least one of the white blood cells detected by the white blood cell detector; and
a processor and a memory storing a computer program that configures the processor to perform operations comprising:
identifying each of nucleus areas of the white blood cells based on the cell images;
classifying the white blood cells into a plurality of types; and
determining a staining abnormality by:
determining first luminance values of each of the identified nucleus areas of the white blood cells, generating a first average value of the determined first luminance values and comparing the first average value with a stored acceptable range;
determining second luminance values of backgrounds of each of the cell images, generating a second average value of the determined second luminance values and comparing the second average value with a stored reference value; and
outputting an error indication of the staining abnormality in response to a first comparison result of the first average value falling outside the acceptable range and an error indication of the light intensity abnormality in response to a second comparison result representing the second average value being equal to or smaller than the reference value.

13. The blood stain sample imaging apparatus of claim 12, wherein the error indication of the light intensity abnormality outputs an error screen on an image display section to replace the light source when the second average value is equal to or smaller than the reference value.

14. The blood stain sample imaging apparatus of claim 12, wherein each of the first and second luminance values is a luminance value of a specific color component.

15. The blood stain sample imaging apparatus of claim 14, wherein the specific color component is a green component.

16. The blood stain sample imaging apparatus of claim 15, wherein the white blood cell associated with the identified nucleus area for determining the first luminance value is a neutrophil.

17. The blood stain sample imaging apparatus of claim 14, wherein the white blood cell associated with the identified nucleus area for determining the first luminance value is a neutrophil.

18. The blood stain sample imaging apparatus of claim 12, wherein the white blood cell associated with the identified nucleus area for determining the first luminance value is a neutrophil.

19. The blood stain sample imaging apparatus of claim 12, wherein the computer program configures the processor to perform operations further comprising correcting Red-Green-Blue values of each of the cell images to adjust for a luminance background of the cell images to reach a predetermined value.

* * * * *